(12) United States Patent
Murata et al.

(10) Patent No.: US 10,674,905 B2
(45) Date of Patent: Jun. 9, 2020

(54) OCT APPARATUS

(71) Applicant: NIDEK CO., LTD., Gamagori, Aichi (JP)

(72) Inventors: Keiji Murata, Aichi (JP); Yusuke Ando, Aichi (JP); Sasagu Tachibana, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 84 days.

(21) Appl. No.: 15/941,902

(22) Filed: Mar. 30, 2018

(65) Prior Publication Data

US 2018/0289256 A1    Oct. 11, 2018

(30) Foreign Application Priority Data

Mar. 31, 2017  (JP) ................................ 2017-070039
Mar. 31, 2017  (JP) ................................ 2017-070040

(51) Int. Cl.
*A61B 3/10*       (2006.01)
*A61B 3/12*       (2006.01)
*A61B 5/00*       (2006.01)

(52) U.S. Cl.
CPC ............ *A61B 3/102* (2013.01); *A61B 3/1225* (2013.01); *A61B 5/0066* (2013.01)

(58) Field of Classification Search
CPC ...... A61B 3/102; A61B 5/0066; A61B 3/1225
See application file for complete search history.

(56) References Cited

U.S. PATENT DOCUMENTS

2016/0038023 A1    2/2016  Endo et al.

FOREIGN PATENT DOCUMENTS

| JP | 2016-32609 A | 3/2016 |
| JP | 2016-209529 A | 12/2016 |
| WO | 2016/178298 A1 | 11/2016 |

*Primary Examiner* — Jack Dinh
(74) *Attorney, Agent, or Firm* — Sughrue Mion, PLLC

(57) ABSTRACT

An OCT apparatus includes an OCT optical system guiding measurement light to a region including a central portion and a peripheral portion of a fundus, and an image processor processing a spectral interference signal output from the OCT optical system to acquire OCT data of an examinee's eye. The OCT optical system includes a first reference optical path having a path length for obtaining OCT data including the central portion and a second reference optical path having a path length for obtaining OCT data including the peripheral portion. The image processor obtains OCT data including the central portion based on an interference signal between measurement light guided to the central portion and reference light from the first reference optical path, and obtains OCT data including the peripheral portion based on an interference signal between measurement light guided to the peripheral portion and reference light from the second reference optical path.

14 Claims, 26 Drawing Sheets

First OCT data

ZD1

Second OCT data

ZD2

OCT APPARATUS

CROSS-REFERENCE TO RELATED APPLICATION

This application claims priority from Japanese Patent Application No. 2017-070039 filed on Mar. 31, 2017 and Japanese Patent Application No. 2017-070040 filed on Mar. 31, 2017, the entire subject-matter of which is incorporated herein by reference.

TECHNICAL FIELD

The present disclosure relates to an OCT apparatus which obtains OCT data of an examinee's eye fundus.

BACKGROUND

As an OCT apparatus which obtains OCT data of a subject, for example, an apparatus capable of acquiring OCT data by processing a spectral interference signal output from an OCT optical system is known, and in recent years, a configuration for obtaining a wide-angle tomographic image by scanning a central portion and a peripheral portion of the fundus in a wide-range has been disclosed (for example, refer to JP-A-2016-209529).

For example, in the apparatus described in JP-A-2016-209529, an optical path length difference of a k clock interferometer provided separately from an OCT interferometer is set to be equal to or greater than 22 mm, and scanning is performed one time in a wide-range of the fundus.

However, in the case of the above-described configuration, it is indispensable to provide the k clock interferometer. Since the k clock requires high-speed sampling, the detector should also have high speed. However, this causes high cost, and further, high frequencies are generally susceptible to noise, and high-speed k clock is likely to lose stability thereof. Therefore, at a depth away from a high-frequency region, that is, a zero delay position, a decrease in SNR and a sampling error due to jitter tend to occur. In addition, when a user tries to stably detect up to high frequencies, the apparatus becomes more complex and extremely expensive.

SUMMARY

An object of the present disclosure is to provide an OCT apparatus capable of acquiring wide-angle OCT data with excellent signal intensity.

In order to solve the above-described problem, the disclosure includes the following configurations.

(1) An OCT apparatus including:
an OCT optical system that includes a first optical splitter configured to split light from an OCT light source into a measurement optical path and a reference optical path, and a detector configured to detect an interference signal between measurement light guided to a fundus of an examinee's eye through the measurement optical path and reference light from the reference optical path, and that guides the measurement light to a wide-angle region including a central portion and a peripheral portion of the fundus along one transverse direction in which the measurement light traverses the fundus; and
an image processor that processes a spectral interference signal output from the OCT optical system to acquire OCT data of the examinee's eye,
in which the OCT optical system includes the reference optical path including a first reference optical path having an optical path length set for obtaining OCT data including a central portion of the fundus, and a second reference optical path which is different from the first reference optical path and has an optical path length set for obtaining OCT data including the peripheral portion of the fundus, and
the image processor
obtains OCT data including the central portion based on an interference signal between the measurement light guided to the central portion of the fundus and the reference light from the first reference optical path, and
obtains OCT data including the peripheral portion based on an interference signal between the measurement light guided to the peripheral portion of the fundus and the reference light from the second reference optical path.

(2) The OCT apparatus according to the above-described (1),
in which the central portion of the fundus is a region including at least a macular portion and a papilla portion of the fundus, and
the peripheral portion of the fundus is a region including each region outside the both ends of the central portion in the transverse direction.

(3) The OCT apparatus according to the above-described (2),
in which the OCT optical system includes an optical scanner configured to scan the measurement light on the fundus of the examinee's eye, and
the measurement light is scanned in a wide-angle region including the central portion and the peripheral portion of the fundus by one time B scanning performed by the optical scanner, and OCT data including the central portion and OCT data including the peripheral portion are acquired.

(4) The OCT apparatus according to the above-described (1),
in which the detector includes
a first detector configured to detect an interference signal between the measurement light guided to the central portion of the fundus and the reference light from the first reference optical path, and
a second detector configured to be different from the first detector and detect an interference signal between the measurement light guided to the peripheral portion of the fundus and the reference light from the second reference optical path.

(5) The OCT apparatus according to the above-described (1),
in which an optical path length of the first reference optical path is set such that first OCT data is acquired in a state where a choroid layer of the central portion of the fundus is formed on a farther front side than a zero delay position at which the optical path lengths of the measurement light and the reference light are identical to each other.

(6) The OCT apparatus according to the above-described (1),
in which an optical path length of the second reference optical path is set such that second OCT data is acquired in a state where a retina of the peripheral portion of the fundus is formed on a farther inner side than a zero delay position at which the optical path lengths of the measurement light and the reference light are identical to each other.

(7) The OCT apparatus according to the above-described (1),
in which the detector is configured to detect an interference signal between the measurement light guided to an anterior ocular segment of the examinee's eye through the measurement optical path and the reference light from the reference optical path.

an optical path length of the first reference optical path and an optical path length of the second reference optical path are different from each other, one of the first reference optical path and the second reference optical path is set to have an optical path length for obtaining OCT data including a cornea of the examinee's eye, and the other of the first reference optical path and the second reference optical path is set to have an optical path length for obtaining OCT data including a crystalline lens of the examinee's eye.

(8) The OCT apparatus according to the above-described (1), the image processor combines OCT data including the central portion of the fundus and OCT data including the peripheral portion of the fundus to obtain wide-angle OCT data of the fundus.

(9) The OCT apparatus according to above-described (4), further including:

an FPN generation optical system that includes at least one optical member configured to generate FPN being fixed pattern noise on OCT data, and generate an FPN signal being a noise signal which indicates the FPN, in which the first detector and the second detector enable to detect the FPN signal, and the image processor enables to simultaneously acquire two OCT data which are respectively corrected based on the FPN signal.

(10) The OCT apparatus according to the above-described (9), further including:

a second optical splitter configured to split the measurement optical path into an optical path toward the fundus of the examinee's eye and an optical path of the FPN generation optical system, and split reflected light from the fundus and light from the FPN generation optical system into an optical path toward the first detector and an optical path toward the second detector through the first optical splitter, in which a light amount split ratio of the reflected light from the fundus by the second optical splitter has a relationship of "the optical path toward the first detector<the optical path toward the second detector through the first optical splitter".

(11) The OCT apparatus according to the above-described (9), further including:

an optical path length variable device that is disposed in at least one of the first reference optical path and the second reference optical path and changes an optical path length of the reference light, in which, when obtaining OCT data of an anterior ocular segment of the examinee's eye, the optical path length variable device sets the optical path length of the reference light such that the first reference optical path and the second reference optical path have optical path lengths different from each other, and the image processor acquires one of OCT data based on the first detector and OCT data based on the second detector as OCT data including a cornea of the examinee's eye, and acquires the other of the OCT data based on the first detector and the OCT data based on the second detector as OCT data including a crystalline lens of the examinee's eye.

(12) The OCT apparatus according to the above-described (9), further including:

an arithmetic processing section configured to obtain combined OCT data by combining OCT data based on the first detector and OCT data based on the second detector based on FPN detected by the first detector and FPN detected by the second detector.

(13) The OCT apparatus according to the above-described (1), in which an optical path length difference between the first reference optical path and the second reference optical path is set in consideration of an optical path length difference between the central portion and the peripheral portion of the fundus.

(14) The OCT apparatus according to the above-described (1), further including:

an optical path length difference adjuster configured to adjust an optical path length difference between the measurement light and the reference light, in which the optical path length difference adjuster sets an optical path length of the first reference optical path in accordance with an optical path length of the measurement light from the central portion of the fundus, and sets an optical path length of the second reference optical path in accordance with an optical path length of the measurement light from the peripheral portion of the fundus.

(15) An OCT apparatus including:

an OCT optical system that includes an optical splitter configured to split light from an OCT light source into a measurement optical path and a reference optical path, and a detector configured to detect a spectral interference signal between measurement light guided to a subject through the measurement optical path and reference light from the reference optical path; and an image processor that processes a spectral interference signal output from the OCT optical system to acquire OCT data of the subject, in which the OCT optical system includes the reference optical path including a first reference optical path and a second reference optical path which is different from the first reference optical path, the detector includes a first detector configured to detect a first interference signal between the reference light from the first reference optical path and the measurement light, and a second detector configured to be different from the first detector and detect a second interference signal between the reference light from the second reference optical path and the measurement light, the OCT apparatus further includes an FPN generation optical system that includes at least one optical member configured to generate FPN being fixed pattern noise on OCT data, and generate an FPN signal being a noise signal which indicates the FPN, the first detector and the second detector enable to detect the FPN signal, and the image processor enables to simultaneously acquire two OCT data which are respectively corrected based on the FPN signal.

(16) The OCT apparatus according to the above-described (15), further including:

a second optical splitter configured to split the measurement optical path into an optical path toward the subject and an optical path of the FPN generation optical system, and split reflected light from the subject and light from the FPN generation optical system into an optical path toward the first detector and an optical path toward the second detector through the first optical splitter, in which a light amount split ratio of the reflected light from the subject by the second optical splitter has a relationship of "the optical path toward the first detector<the optical path toward the second detector through the first optical splitter".

(17) The OCT apparatus according to the above-described (15), further including:

an optical path length variable device that is disposed in at least one of the first reference optical path and the second reference optical path and changes an optical path length of the reference light.

in which, when obtaining OCT data of a fundus of an examinee's eye being as the subject, the optical path length variable device sets the optical path length of the reference light such that an optical path length of the first reference optical path is substantially identical with an optical path length of the second reference optical path, and the image processor acquires first OCT data based on the first detector and second OCT data based on the second detector as OCT data of an identical region of the fundus, and when obtaining OCT data of an anterior ocular segment of the examinee's eye being as the subject, the optical path length variable device sets the optical path length of the reference light such that the first reference optical path and the second reference optical path have optical path lengths different from each other, and the image processor acquires one of first OCT data based on the first detector and second OCT data based on the second detector as OCT data including a cornea of the examinee's eye, and acquires the other of the first OCT data based on the first detector and the second OCT data based on the second detector as OCT data including a crystalline lens of the examinee's eye.

(18) The OCT apparatus according to the above-described (15), further including:

an arithmetic processing section configured to obtain combined OCT data by combining the first OCT data based on the first detector and the second OCT data based on the second detector based on FPN detected by the first detector and FPN detected by the second detector.

DETAILED DESCRIPTION

Figure 1:
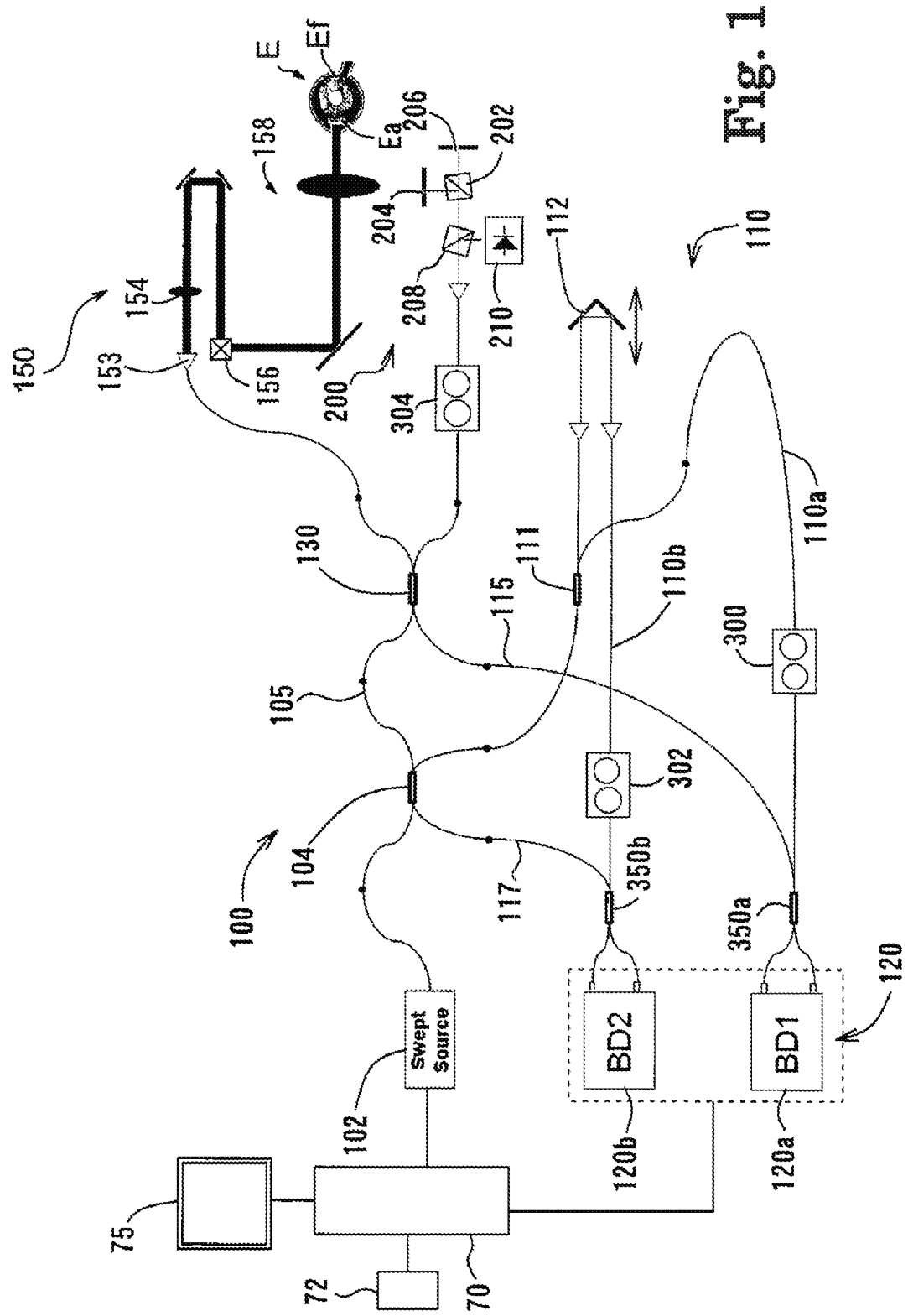
FIG. 1 is a view illustrating an example of an OCT apparatus according to an embodiment.

An example of an embodiment of the present disclosure will be described based on the drawings. FIGS. 1 to 22 are views related to an example of the present embodiment. Meanwhile, items classified as the following sign "< >" may be used independently of or in relation to each other.

The OCT apparatus according to the present embodiment may include an OCT optical system and may be capable of acquiring OCT data by processing a spectral interference signal output from a detector of the OCT optical system. In this case, the OCT optical system may be, for example, a Fourier domain OCT optical system (SS-OCT optical system, SD-OCT optical system), and the OCT optical system may include an optical splitter for splitting light from an OCT light source into a measurement optical path and a reference optical path and may detect the spectral interference signal between measurement light guided to the subject through the measurement optical path and reference light from a reference optical path.

<Fundus Wide-Angle Capturing>

The OCT optical system may be provided for splitting the light from the OCT light source into the measurement optical path and the reference optical path and detecting the interference signal between the measurement light guided to the examinee's eye fundus through the measurement optical path and the reference light from the reference optical path using the detector.

The OCT optical system may be an OCT optical system which is capable of guiding the measurement light in a wide-angle region including a fundus central portion and a fundus peripheral portion in one transverse direction in which the measurement light traverses the fundus. In this case, as the wide-angle region, for example, a wide angular region which traverses both the fundus central portion and the fundus peripheral portion in a case where the measurement light traverses the fundus in a specific transverse direction (for example, in the horizontal direction), may be adopted. In addition, with respect to the transverse region which the measurement light traverses, for example, the transverse region in the fundus central portion in the fundus central portion and the transverse region in the fundus peripheral portion may be continuous with respect to the transverse direction. As the wide-angle region, for example, a region which is equal to or greater than 18 mm on the fundus may be adopted. Naturally, the wide-angle region may be used in a case of obtaining a region narrower than 18 mm, and the apparatus of the present embodiment is particularly useful in a case of capturing a peripheral region of the examinee's eye where the curvature of the fundus is large.

As an OCT optical system which can guide the measurement light in a wide-angle region of the fundus, for example, an objective lens optical system may be used, or an objective mirror optical system using a concave surface mirror may be used. Further, a wide-angle attachment may be attached to the objective lens optical system.

As the fundus central portion, for example, at least a region including the macular portion and the papilla portion of the fundus is set, and as the fundus peripheral portion, a region including each of the regions outside the both end portions of the fundus central portion in one transverse direction may be set. Naturally, not being limited thereto, for example, as the fundus central portion, at least the region including the macular portion of the fundus is set, and as the fundus peripheral portion, a region including each of the regions outside the both end portions of the fundus central portion in one transverse direction may be set.

The OCT optical system may include a plurality of reference optical paths. For example, the OCT optical system includes: a first reference optical path having an optical path length set for obtaining the OCT data including the fundus central portion; and a second reference optical path which is different from the first reference optical path and has an optical path length set for obtaining the OCT data including the fundus peripheral portion. In this case, an optical path length difference between the first reference optical path and the second reference optical path may be set corresponding to an optical path length difference of the measurement light between the fundus central portion and the fundus peripheral portion. In addition, in consideration of the curvature of the eyeball, for example, the second reference optical path may be set to have a shorter optical path length than that of the first reference optical path.

The OCT apparatus according to the present embodiment may include an image processor, and the image processor may be capable of acquiring the OCT data by processing a spectral interference signal output from the OCT optical system.

In this case, for example, the image processor may obtain the OCT data including the fundus central portion based on the interference signal between the measurement light guided to the fundus central portion and the reference light from the first reference optical path, and may obtain the OCT data including the fundus peripheral portion based on the interference signal between the measurement light guided to the fundus peripheral portion and the reference light from the second reference optical path. In this case, for example, the OCT data including the fundus central portion and the OCT data including the fundus peripheral portion may be continuous in at least one of the transverse direction and the depth direction.

According to this, for example, by providing the reference optical path that corresponds to the fundus central portion and the reference optical path that corresponds to the fundus peripheral portion, for example, it is possible to acquire the OCT data in the wide-angle region with excellent signal intensity.

In addition, the image processor may combine the OCT data including the fundus central portion and the OCT data including the fundus peripheral portion and may obtain wide-angle OCT data of the examinee's eye fundus. According to this, one piece of wide-angle OCT data can be obtained.

The OCT optical system may include an optical scanner for scanning the measurement light on the examinee's eye fundus. In this case, the optical scanner may scan the wide-angle region including the fundus central portion and the fundus peripheral portion by scanning the measurement light on the fundus in one scanning direction. In this case, for example, a scanning region in the fundus central portion and a scanning region in the fundus peripheral portion may be continuous in the transverse direction. In addition, the optical scanner may be configured, for example, to be capable of scanning the measurement light until achieving a scan angle at which it is possible to scan the wide-angle range on the fundus. Further, the optical scanner may be disposed, for example, substantially at a position conjugated to the pupil of the examinee's eye, and may measure the measurement light with the center of the pupil as a pivot point.

In a case where the optical scanner is provided, the measurement light is scanned in the wide-angle region including the fundus central portion and the fundus peripheral portion by one time B scanning performed by the optical scanner, and the OCT data including the fundus central portion and the OCT data including the fundus peripheral portion may be acquired. According to this, for example, the OCT data in the wide-angle region can be acquired smoothly.

The OCT optical system may include, for example, a first detector that corresponds to the fundus central portion and a second detector that corresponds to the fundus peripheral portion. In this case, the OCT optical system includes: a first detector for detecting the interference signal between the measurement light guided to the fundus central portion and the reference light from the first reference optical path; and a second detector which is different from the first detector and detects the interference signal between the measurement light guided to the fundus peripheral portion and the reference light from the second reference optical path. According to this, for example, since the first detector and the second detector can be used in parallel, the OCT data of the fundus central portion and the fundus peripheral portion can be reliably detected, and each piece of the OCT data can be acquired with smooth and excellent signal intensity.

<Optical Path Length of Reference Optical Path>

In addition, in the first reference optical path, for example, an optical path length may be set such that first OCT data is acquired in a state where a choroid layer of the fundus central portion is formed on the farther front side than a zero delay position at which the optical path lengths of the measurement light and the reference light are identical to each other. According to this, for example, it is possible to reduce mixing of a mirror image and a real image in the first OCT data, and to improve the contrast on the choroid layer side.

In addition, in the second reference optical path, for example, an optical path length may be set such that second OCT data is acquired in a state where the retina of the fundus peripheral portion is formed on the farther inner side than the zero delay position at which the optical path lengths of the measurement light and the reference light are identical to each other. According to this, for example, it is possible to reduce mixing of a mirror image and a real image in the second OCT data, and to reduce influence of deterioration of light amount in the fundus peripheral portion.

In addition, by setting the first reference optical path and the second reference optical path as described above, it is possible to reduce the mixing of the mirror image in the first OCT data and the second OCT data, and to obtain the entire OCT data in the wide-angle region with excellent signal intensity.

In addition, the first reference optical path and the second reference optical path are not limited to the above-described configuration. In the first reference optical path, for example, the optical path length may be set to be an optical path length such that the first OCT data in a state where the retina of the fundus central portion is formed on the father inner side than the zero delay position is acquired, and for example, in the second reference optical path, the optical path length may be set such that the second OCT data in a state where the choroid layer of the fundus peripheral portion is formed on the farther front side than the zero delay position is acquired.

The OCT optical system may further be capable of detecting the interference signal of the measurement light guided to an anterior ocular segment of the examinee's eye through the measurement optical path and the reference light from the reference optical path by the detector. In this case, the first reference optical path and the second reference optical path may be set to have optical path lengths different from each other, one of the first reference optical path and the second reference optical path may be set to have an optical path length for obtaining the OCT data including the cornea (for example, the cornea and the crystalline lens front surface) of the examinee's eye, and the other of the first reference optical path and the second reference optical path may be set to have an optical path length for obtaining the OCT data including the crystalline lens (for example, the crystalline lens rear surface) of the examinee's eye. According to this, in addition to the OCT data in the wide-angle region, the OCT data in a wide-range of the anterior ocular segment can be acquired with excellent signal intensity.

In addition, in the above-described description, two reference optical paths that correspond to the fundus central portion and the fundus peripheral portion are provided, but the invention is not limited thereto, and three or more reference optical paths may be provided. For example, the entire fundus is split into the fundus central portion, a first fundus peripheral portion outside the fundus central portion, and a second fundus peripheral portion outside the first fundus peripheral portion, and a first reference optical path that corresponds to the fundus central portion, a second reference optical path that corresponds to the first fundus peripheral portion, and a third reference optical path that corresponds to the second fundus peripheral portion, are provided.

In addition, the optical path lengths of the two reference optical paths may be adjusted, and a first wide-angle capturing mode in which the first reference optical path that corresponds to the fundus central portion and the second reference optical path that corresponds to the first fundus peripheral portion are set, and a second wide-angle capturing mode in which the first reference optical path that corresponds to the fundus central portion or the first fundus peripheral portion and the second reference optical path that corresponds to the second fundus peripheral portion are set, may be switchable to each other.

<Plurality of Detectors and FPN Optical System>

The OCT optical system may include a plurality of reference optical paths, and for example, may include the first reference optical path and the second reference optical path which is different from the first reference optical path. In this case, for example, the OCT optical system may include: a first detector for detecting a first interference signal between the reference light guided from the first reference optical path and the measurement light; and a second detector which is different from the first detector and detects a second interference signal between the reference light from the second reference optical path and the measurement light.

<FPN Optical System>

The OCT optical system may be provided with an FPN generation optical system for generating an FPN signal, and for example, the FPN generation optical system may include at least one optical member for generating the FPN. The FPN generation optical system may be disposed in the measurement optical path or in the reference optical path. In addition, the FPN is fixed pattern noise, and for example, the FPN signal is generated as a noise signal having a fixed pattern on the OCT data.

At least one of the first detector and the second detector can detect the FPN signal and can correct the OCT data using the FPN signal (for example, image composition or correction of the mapping state). By using the FPN signal, excellent OCT data can be obtained. In this case, both the first detector and the second detector may be capable of detecting the FPN signal, and accordingly, it is possible to perform processing using the FPN signal with higher accuracy.

<Second Optical Splitter>

The OCT optical system may include a second optical splitter, and for example, the second optical splitter may be provided for splitting the measurement optical path into an optical path toward the subject and an optical path of the FPN generation optical system. For example, the second optical splitter may further split the light from the subject and the light from the FPN generation optical system into an optical path toward the first detector and the optical path toward the second detector through the first optical splitter.

Here, the OCT optical system includes a first optical path which guides reflected light from the subject to the first detector through the second optical splitter not through the first optical splitter, and a second optical path which guides the reflected light from the subject to the second detector through the second optical splitter and the first optical splitter, and accordingly, the reflected light from the subject can be efficiently guided to the plurality of detectors.

In addition, the OCT optical system is not limited to the above-described configuration, and a configuration in which an optical path which guides the reflected light from the subject to the first detector and the second detector through the second optical splitter not through the first optical splitter may be adopted, and in this case, the OCT optical system may include a third optical splitter which splits the reflected light from the subject into the optical path toward the first detector and the optical path toward the second detector further on the detector side than the second optical splitter.

<Light Amount Split Ratio>

With respect to the light amount split ratio of the reflected light from the subject by the above-described second optical splitter, the light amount split ratio may be set such that the optical path toward the first detector to be smaller than the optical path toward the second detector through the first optical splitter. According to this, it is possible to detect the first interference signal detected by the first detector and the second interference signal detected by the second detector with an appropriate balance.

In addition, with respect to the light amount split ratio of the second optical splitter, the light amount split ratio may be set such that the optical path toward the light source to be smaller than the optical path toward the second detector. According to this, the reflected light from the subject can be efficiently guided to the second detector.

In addition, as a result, the light amount split ratios of the first optical splitter and the second optical splitter may be set such that the light amount ratios of the optical path toward the first detector and the optical path toward the second detector are the same as each other. According to this, since it is possible to make the intensity of the first interference signal and the second interference signal uniform, and as a result, it is possible to acquire excellent OCT data based on each of the interference signals.

In addition, with respect to the light amount split ratios of the first optical splitter and the second optical splitter, taking into consideration the difference in amount of reflected light at a capturing part of the OCT data detected by the first detector and the second detector, the light amount split ratio may be set.

<Image Composition Using FPN>

The OCT apparatus may include an arithmetic processing section (for example, a processor) for acquiring the OCT data of the subject by processing the spectral interference signal output from the OCT optical system. In this case, the arithmetic processing section may obtain combined OCT data, for example, by combining the first OCT data based on the first interference signal and the second OCT data based on the second interference signal, based on the FPN detected by the first detector and the FPN detected by the second detector. According to this, a plurality OCT data can be combined with high accuracy. By the composition, a region which is not sufficient with one piece of OCT data is compensated.

In this case, the arithmetic processing section can obtain the relative position information of the two OCT data by using the FPN generated by the optical member for FPN generation to combine the OCT data, and can accurately combine the data. For example, the arithmetic processing section may use the FPN generated by the surface reflection of the optical member for FPN generation to combine the OCT data, and as a result, it is possible to mitigate deterioration of the signal intensity (SNR) of the FPN. Naturally, the arithmetic processing section may combine the OCT data using the FPN generated by rear surface reflection or a surface to which coating is performed, and in this case, the signal intensity is attenuated, but constant effects can be obtained for data composition.

In the above-described configuration, for example, the FPN generation optical system may be an FPN generation optical system which includes at least a first optical member which generates a first FPN and a second optical member which generates a second FPN at a position different from that of the first FPN, and generates at least two FPN signals.

In this case, the arithmetic processing section may obtain the combined OCT data, for example, by combining the first OCT data based on the first interference signal and the second OCT data based on the second interference signal, based on the FPN by the first optical member which is detected by the first detector and the FPN by the second optical member detected by the second detector. According to this, for example, a capturing range in the depth direction can be widened. In this case, for example, the first OCT data and the second OCT data may be positioned based on the separation between the FPN by the first optical member and the FPN by the second optical member.

For example, in a case of capturing a certain range of parts common to the two OCT systems, it is possible to reduce overlapping regions between different data. Furthermore, there may be discontinuous regions between the two capturing regions. When capturing the anterior ocular segment, the first OCT data may include from the cornea front surface to the crystalline lens front surface, and the second OCT data may be configured to include only a crystalline lens rear surface. Such a configuration is particularly useful in a case where a depth range is different by changing detectors with two OCT systems.

In addition, the FPN generation optical system may include an optical path splitting member, and the first optical member may be disposed in the first optical path split by the optical path splitting member, and the second optical member may be disposed in the second optical path split by the optical path splitting member. In a case of using two FPN signals, used, since signals with low sensitivity will degrade accuracy, it is preferable that each signal intensity is high to the same extent, and according to this, it is possible to independently control the light from each of the optical members. In this case, for example, the first optical path and the second optical path have optical path lengths different from each other, and a dispersion amount of the first optical path may be equal to the dispersion amount of the second optical path. According to this, the influence of dispersion in each of the FPN signals can be made uniform, each of the FPN signals can be uniformly detected, and image composition can be performed with high accuracy. Further, a case where the optical path length difference is small to the extent that both the first and second OCT data are accommodated in an acquisition range, may be more appropriate. By acquiring both the first and second OCT data accommodated in the acquisition range and analyzing the OCT data, it is possible to calibrate the separation of two FPNs at any timing. For example, the position itself of the FPN varies depending on the use environment (temperature or the like) of the apparatus, and it is also conceivable that the separation of the FPN also fluctuates due to the influence of the wavelength shift or the like due to aged deterioration of the light source. However, by using separation information between the FPNs when performing the composition according to the present embodiment, or by measuring and calibrating the separation information at any timing, it is possible to maintain the image to be combined long and stably.

In addition, the first optical path and the second optical path have optical path lengths different from each other within a range included in the depth-range of at least one of the OCT channels, and the dispersion amount of the first optical path and the dispersion amount of the second optical path may be equal to each other. According to this, it is possible to perform calibration on one OCT channel with high accuracy.

In addition, in the above-described description, data composition using the FPN generation optical system for generating at least two FPN signals is illustrated, but the invention is not limited thereto, and for example, the arithmetic processing section may generate different OCT data by using the FPN signal by one common optical member. In this case, the configuration of the FPN generation optical system can be simplified.

<Wavenumber Mapping Correction>

The arithmetic processing section may use the FPN signal both in combining the OCT data and in acquiring the correction information for correcting the mapping state of each wavenumber component. According to this, it is possible to acquire the correction information of the wavenumber mapping with high accuracy, and to appropriately acquire the combined OCT data.

In this case, for example, the arithmetic processing section processes the FPN signal detected by the first detector and the second detector, and based on the mapping information of each of the wavenumber components based on the FPN signal, the correction information for correcting a mapping state of each of the wavenumber components can be obtained, and the first OCT data based on the first interference signal and the second OCT data based on the second interference signal may be acquired by using the correction information. Furthermore, the arithmetic processing section may combine the data based on the FPN detected by the first detector and the FPN detected by the second detector.

<Polarization Adjustment Mechanism>

For example, a polarization adjustment section (polarizer) may be provided in the optical path of the OCT optical system, and the polarization adjustment section may be provided to adjust the polarization state of at least one of the measurement light and the reference light. The polarization adjustment section may be disposed in at least one of the optical path of the measurement light and the optical path of the reference light. In addition, the polarization adjustment section is disposed in the optical path after the optical path of the measurement light and the optical path of the reference light are branched, and may be used for matching the polarization state of the measurement light and the reference light.

For example, the polarization adjustment section may adjust the polarization direction by rotating an optical fiber in the optical path or by applying pressure. In addition, in the polarization adjustment section, the polarization direction may be adjusted by using a half wave plate or a quarter wave plate. In addition, the polarization adjustment section may be realized by combining a prism (for example, Fresnel lens) having the same effect as the half wave plate or the quarter wave plate. In addition, the polarization adjustment section may be configured to be capable of adjusting the polarization direction at least between linearly polarized light of S-polarized light, linearly polarized light of P-polarized light, and circularly polarized light.

The polarization adjustment section may be disposed, for example, in at least one of the first reference optical path and the second reference optical path, and may adjust the polarization state of the reference light. In this case, for example, a plurality of polarization adjustment sections may be provided, and in a first example, the polarization adjustment sections are disposed in the first reference optical path and the second reference optical path respectively, and may adjust the polarization state of the reference light passing through the first reference optical path and the polarization state of the reference light passing through the second reference optical path respectively. Further, in a second example, the polarization adjustment section is disposed in one of the first reference optical path and the second reference optical path and in the measurement optical path, and may adjust the polarization state of the reference light passing through one of the first reference optical path and the second reference optical path and the polarization state of the measurement light passing through the measurement optical path respectively. By providing a plurality of polarization adjustment sections in this manner, for example, the first OCT data based on the first detector and the second OCT data based on the second detector can be appropriately detected respectively.

In the OCT apparatus, a polarization control section which controls the polarization adjustment section may be provided, and for example, the control section may control a plurality of polarization adjustment sections and may adjust the polarization state such that each of the first OCT data based on the first detector and the second OCT data based on the second detector satisfies a predetermined allowable condition. In this case, the predetermined allowable condition may be, for example, a state where the OCT data has reached a predetermined signal intensity, or a state where the signal intensity of the OCT data has reached the vicinity of the peak. In this case, by adjusting the polarization state based on the first OCT data and by adjusting the polarization state based on the second OCT, each piece of OCT data can be acquired in an excellent state. In this case, for example, each time the polarization state is changed, an evaluation value for evaluating the signal intensity may be calculated and the polarization state may be adjusted based on the evaluation value.

In addition, for example, the polarization control section may control the polarization adjustment section and may adjust the polarization state such that a signal intensity ratio between the FPN detected by the first detector and the FPN detected by the second detector satisfies a predetermined allowable condition. In this case, the predetermined allowable condition may be, for example, a state where the signal intensity ratio has reached a predetermined signal intensity, or a state where the difference in signal intensity is the smallest. In this case, for example, each time the polarization state is changed, an evaluation value for evaluating the signal intensity may be calculated and the polarization state may be adjusted based on the evaluation value. In addition, in a case where the dispersion of the FPN signal is equal in the first or second OCT data, evaluation may be performed based on the degree of similarity of signal spread (PSF). For example, each FPN has a specific sidelobe depending on the distribution of the light source, but when coefficient multiplication is performed such that the peak heights match each other, the matching degree of polarization may be determined depending on the degree of correlation (overlapping degree) therebetween.

In addition, the polarization adjustment section may be disposed, for example, in the optical path of the FPN generation optical system and may be provided to adjust the polarization state of the light passing through the FPN generation optical system. In this case, for example, the polarization control section may control the polarization adjustment section and may adjust the signal intensity of the FPN signal acquired in one of the two OCT systems. According to this, since the FPN signal can be acquired with an appropriate signal intensity, various types of processing using the FPN signal can be appropriately performed. In a case where the other OCT system has one more polarization adjustment member, the FPN may control the polarization and adjust the polarization according to a predetermined intensity ratio or PSF characteristics.

Examples

In the present example, an optical coherence tomography (OCT) apparatus illustrated in FIG. 1 is used as the OCT apparatus. The OCT apparatus according to the present example basically includes, for example, a wavelength sweep type OCT (SS-OCT: swept source-OCT), and for example, includes a wavelength variable light source 102, an interference optical system (OCT optical system) 100, an arithmetic controller (arithmetic control section) 70. In addition, the OCT apparatus may be provided with a memory 72, a display section 75, a front image observation system (not illustrated) and a fixation target projection system. The arithmetic controller (hereinafter, control section) 70 is connected to the wavelength variable light source 102, the interference optical system 100, the memory 72, and the display section 75.

The interference optical system 100 guides the measurement light to an eye E by a light guiding optical system 150. The interference optical system 100 guides the reference light to a reference optical system 110. The interference optical system 100 causes a detector (light receiving element) 120 to receive the interference signal light acquired by the interference between the measurement light reflected by the eye E and the reference light. Furthermore, the interference optical system 100 of the present example includes an FPN generation optical system 200 (will be described in detail later). In addition, the interference optical system 100 is mounted in a housing (apparatus main body) which is not illustrated, and the housing is moved three-dimensionally with respect to the eye E by a well-known alignment movement mechanism via an operation member, such as a joystick, and accordingly, alignment with respect to the examinee's eye may be performed.

An SS-OCT method is used for the interference optical system 100, and the wavelength variable light source (wavelength scanning type light source) which changes the emitted wavelength at a high speed in time is used as the light source 102. The light source 102 is configured with, for example, a laser medium, a resonator, and a wavelength selection filter. In addition, examples of the wavelength selection filter include a combination of a diffraction grating and a polygon mirror, and a filter using a Fabry-Perot etalon. In addition, as the light source 102, a VCSEL type wavelength variable light source may be used.

A coupler (splitter) 104 is used as the first optical splitter and splits the light emitted from the light source 102 into the measurement optical path and the reference optical path. For example, the coupler 104 guides the light from the light source 102 to an optical fiber 105 on the measurement optical path side and guides the light to the reference optical system 110 on the reference optical path side.

A coupler (splitter) 130 is used as the second optical splitter and splits the light (measurement light) from the optical fiber 105 into the optical path of the light guiding optical system 150 and the optical path of the FPN generation optical system 200. In other words, in the measurement optical path, the light guiding optical system 150 and the FPN generation optical system 200 are provided. The coupler (splitter) 130 may be a beam splitter or a circulator.

<Light Guiding Optical System>

The light guiding optical system 150 is provided to guide the measurement light to the eye E. In the light guiding optical system 150, for example, an optical fiber 152, a coupler 153, a collimator lens 154, an optical scanner 156, and an objective lens system 158 may be sequentially provided. In this case, the measurement light becomes a parallel beam by the collimator lens 154 through the optical fiber 152 and the coupler 153, and is toward the optical scanner 156. The eye E is irradiated with the light passing through the optical scanner 156 through the objective lens system 158. Both the anterior ocular segment and the posterior ocular segment are irradiated with the measurement light, and is scattered and reflected by each tissue.

The optical scanner 156 may cause the measurement light to scan in the X and Y directions (transverse direction) on the eye E. The optical scanner 156 is, for example, two Galvano mirrors, and a reflection angle thereof is voluntarily adjusted by a driving mechanism. The luminous flux emitted from the light source 102 has the reflection (traveling) direction changed, and is scanned in any direction on the fundus. As the optical scanner 156, for example, an acousto-optical modulator (AOM) or the like for changing the traveling (deflection) direction of light may be used in addition to the reflecting mirror (Galvano mirror, polygon mirror, or resonant scanner).

In this case, the scattering light (reflected light) from the eye E by the measurement light passes through the objective lens system 158, the optical scanner 156, the collimator lens 154, the coupler 153, and the optical fiber 152, and then reaches the coupler 130. The coupler 130 splits the light from the optical fiber 152 into an optical path (for example, an optical fiber 115 to a coupler 350a) toward a first detector 120a and an optical path (for example, the optical fiber 105, the coupler 104, and an optical fiber 117 to a coupler 350b) toward a second detector 120b.

In the measurement light split by the coupler 130, the measurement light that has passed through the optical path toward the first detector 120a is combined with the reference light from a first reference optical path 110a by the coupler 350a to interfere. In addition, the measurement light that has passed through the optical path toward the second detector 120b is combined with the reference light from a second reference optical path 110b by the coupler 350b to interfere.

<Reference Optical System>

The reference optical system 110 generates the reference light combined with the reflected light acquired by the reflection of the measurement light in the eye E. The reference light that has passed through the reference optical system 110 is combined with the light from the measurement optical path by the coupler (for example, the couplers 350a and 350b) to interfere. The reference optical system 110 may be a Michelson type or a Mach-Zehnder type.

The reference optical system 110 may be formed, for example, by a reflection optical system and may guide the light from the coupler 104 to the detector 120 by reflecting the light with the reflection optical system. The reference optical system 110 may be formed by a transmission optical system. In this case, the reference optical system 110 guides the light to the detector 120 by transmitting the light from the coupler 104 without returning the light.

In addition, an optical member for adjusting the optical path length difference between the measurement light and the reference light may be disposed in at least one of the measurement optical path and the reference optical path. For example, by integrally moving the collimator lens 154 and the coupler 153, the optical path length of the measurement light may be adjusted, and as a result, the optical path length difference between the measurement light and the reference light may be adjusted. Naturally, the optical member disposed in the reference optical path is moved, and as a result, the optical path length difference between the measurement light and the reference light may be adjusted.

In the present example, a plurality of reference optical paths may be provided as the reference optical system 110, and for example, the first reference optical path 110*a* and the second reference optical path 110*b* may be provided.

The reference optical system 110 may be provided with, for example, an optical splitter (for example, a coupler 111) for splitting the reference optical path into the first reference optical path 110*a* and the second reference optical path 110*b*. For at least one of the first reference optical path 110*a* and the second reference optical path 110*b*, for example, an optical member 112 which is moved to change the optical path length of the reference light may be provided. The optical member 112 may be moved by a driving section (not illustrated) controlled by the control section 70.

For example, the reference light from the coupler 104 is split by the coupler 111 into the first reference optical path 110*a* and the second reference optical path 110*b*. The reference light that has passed through the first reference optical path 110*a* is combined with the measurement light from the optical fiber 115 by the coupler 350*a* to interfere. The reference light that has passed through the second reference optical path 110*b* is combined with the measurement light from the optical fiber 117 by the coupler 350*b* to interfere.

The first reference optical path 110*a* and the second reference optical path 110*b* may be set to have optical path lengths different from each other. According to this, for example, interference signals that correspond to depth regions different from each other can be acquired at the same time, and as a result, a wide-range of OCT data can be simultaneously acquired.

For example, the first reference optical path 110*a* may be provided to obtain an interference signal that corresponds to a first depth region (for example, the crystalline lens and the fundus) in the examinee's eye, and the second reference optical path 110*b* may be provided to obtain an interference signal that corresponds to a second depth region (for example, the cornea) in the examinee's eye. In this case, the second depth region is set to a region different from the first depth region. In this case, the first depth region and the second depth region may be regions separated from each other, may regions adjacent to each other, or may be regions which overlap each other.

In addition, the first reference optical path 110*a* and the second reference optical path 110*b* may be set to have the same optical path lengths. According to this, for example, interference signals that correspond to the same depth region can be acquired at the same time, and as a result, the plurality of OCT data related to the same region can be simultaneously acquired.

<Photodetector>

The detector 120 is provided for detecting interference by the light from the measurement optical path and the light from the reference optical path. In addition, the detector 120 may be a light receiving element, for example, a point sensor including only one light receiving portion, and for example, an avalanche photo diode may be used.

In the present example, as the detector 120, the first detector 120*a* and the second detector 120*b* different from the first detector 120*a* may be provided. The first detector 120*a* may be provided as a detector for detecting the first interference signal between the reference light from the first reference optical path 110*a* and the measurement light from the optical fiber 115. The second detector 120*b* may be provided as a detector for detecting the second interference signal between the reference light from the second reference optical path 110*b* and the measurement light from the optical fiber 117. In this case, by detecting the first interference signal with the first detector 120*a* and at the same time detecting the second interference signal with the second detector 120*b*, the first interference signal and the second interference signal can be simultaneously detected. The sampling speeds of the detectors may be different from each other or may be the same as each other.

In addition, the first detector 120*a* and the second detector 120*b* may be balanced detectors, respectively. In this case, each of the first detector 120*a* and the second detector 120*b* includes a plurality of light receiving elements, obtains the difference between the interference signal from the first light receiving element and the interference signal from the second light receiving element, and can reduce unnecessary noise included in the interference signal.

<FPN Generation Optical System>

The FPN generation optical system 200 may be provided to generate the FPN signal. The FPN generation optical system 200 may include at least one optical member (for example, a first optical member 204 or a second optical member 206) for generating the FPN. In the present example, the FPN generation optical system 200 is disposed at a position branched from the optical path in which the measurement light is toward the examinee's eye.

As the FPN generation optical system 200, for example, the reflection optical system may be used, and for example, as the FPN generation optical member, for example, a light reflecting member (for example, a mirror) may be used. In addition, in the present example, a plurality of optical members for generating the FPN are provided, but the invention is not limited thereto, and the FPN generation optical system 200 may be configured to have one optical member for generating the FPN.

The FPN signal is detected by the first detector 120*a* together with the first interference signal, and the FPN signal is detected by the second detector 120*b* together with the second interference signal. The FPN signal includes, for example, a composition of the first OCT data based on the first interference signal and the second OCT data based on the second interference signal (which will be described in detail later), wavenumber mapping correction of each of the interference signals, polarization adjustment and the like may be used.

For example, the FPN generation optical system 200 may be provided to generate a first FPN signal and a second FPN signal. For example, the FPN generation optical system 200 may include at least the first optical member 204 for generating the first FPN or the second optical member 206 for generating the second FPN. The second optical member 206 may be disposed such that the light that has passed through the second optical member has an optical path length different from the optical path length due to the light that has passed through the first optical member 204. According to this, the second FPN is generated at a position different from that of the first FPN. In addition, the zero delay position which will be described later corresponds to the position at which the optical path length of the measurement light is identical to the optical path length of the reference light on the OCT data.

By using the first optical member 204 and the second optical member 206 at the same time, it is possible to simultaneously generate two FPN signals, and according to this, it is possible to reduce the influence of the time shift when processing the two FPN signals. In addition, the FPN optical system 200 may include three or more FPN generation optical members, and by using the members at the same time, it is possible to simultaneously generate three or more FPN signals.

As the FPN generation optical system 200, for example, the reflection optical system may be used, and for example, as the FPN generation optical member, for example, a light reflecting member (for example, a mirror) may be used. In the present example, mirrors are used as the first FPN generation optical member 204 and the second FPN generation optical member 206, but the invention is not limited thereto.

In this case, after the light from the coupler 130 passes through the first optical member 204 or the second optical member 206, the light returns to the coupler 130, passes through the path similar to the light from the light guiding optical system 150, and reaches the coupler 350a and the coupler 350b. The light from the FPN generation optical system 200 is combined with the reference light at the couplers 350a and 350b to interfere. In addition, the optical path length from the light source 102 and the FPN generation optical system 200 to the couplers 350a and 350b, and the optical path length from the light source 102 and the reference optical system 110 to the couplers 350a and 350b may be set to substantially the same length.

For example, as the light that has passed through the first optical member 204 interferes with the reference light, the interference signal light that corresponds to the first FPN is generated, the first FPN signal is generated in the detector 120, the light that has passed through the second optical member 206 interferes with the reference light, and accordingly, the interference signal light that corresponds to the second FPN is generated, and the second FPN signal is generated in the detector 120. As a result, for example, both the first FPN signal and the second FPN signal are simultaneously detected by the detector 120.

In a case where the FPN signal is used in predetermined processing, in each of the detector 120a and the detector 120b, both of the first FPN signal and the second FPN signal may be simultaneously detected, one FPN signal may be detected by the detector 120a, and the other FPN signal may be detected and by the detector 120b. In addition, both the first FPN signal and the second FPN signal are simultaneously detected in one of the detector 120a and the detector 120b, and one of the first FPN signal and the second FPN signal may be detected in the other of the detector 120a and the detector 120b. In addition, at least one FPN signal is detected in one of the detector 120a and the detector 120b, and the FPN signal may not be detected in the other of the detector 120a and the detector 120b.

In addition, a light amount monitor 210 may be disposed in the FPN generation optical system 200, and the light from the light source 102 is detected by the light amount monitor 120 through a beam splitter 208. An output signal from the light amount monitor 120 may be used for determining whether or not the amount of emitted light of the light source 102 is appropriate.

<Light Amount Branching Ratio>

Here, the coupler 130 splits the light from the coupler 104 into the optical path of the light guiding optical system 150 and the optical path of the FPN generation optical system 200, and also splits the light from the light guiding optical system 150 and the FPN generation optical system 200 into the optical path (for example, optical fiber 115 to coupler 350a) toward the first detector 350a and the optical path toward the coupler 104 (for example, the optical fiber 105, the coupler 104, and the optical fiber 117 to the coupler 350b).

A light amount split ratio S1 of the coupler 130 when splitting the light from the fiber 105 may be set such that more amount of light is guided to the FPN generation optical system 200 than the light guiding optical system 150. In this case, the light amount ratio at which the light from the fiber 105 is split by a coupler 130 is smaller in the light guiding optical system 150 that in the FPN generation optical system 200.

A light amount split ratio S2 of the coupler 130 when splitting the light from the light guiding optical system 150 depends on the light amount split ratio S1. As a result, regarding the light from the light guiding optical system 150, more amount of light is guided to the optical path toward the second detector 120a than the optical path toward the first detector 120a. In this case, the light amount ratio at which the light from the light guiding optical system 150 is split by the coupler 130 is smaller in the optical path toward the first detector 120a than in the optical path toward the coupler 104.

The measurement light that has passed through the optical path toward the first detector 120a interferes with the light from the first reference optical path 110a and then is detected as the first interference signal by the first detector 120a. Meanwhile, the measurement light toward the coupler 104 is split by the coupler 104 into the optical path toward the light source 102 and the optical path (for example, the optical fiber 117 to the coupler 350b) toward the second detector 120b. A light amount split ratio S4 when splitting the light from the coupler 130 depends on the light amount split ratio S3 when splitting the light from the light source 102 into the measurement optical path and the reference optical path. In a case where the light amount split ratio S3 is set such that more amount of light is guided to the reference optical path than that in the measurement optical path, the light amount ratio at which the light from the coupler 130 is split by the coupler 104 is smaller in the optical path toward the light source 102 than in the optical path toward the second detector 120b. As a result, regarding the light from the coupler 130, more amount of light is guided to the optical path toward the second detector 120b than the optical path toward the light source 102. The measurement light that has passed through the optical path toward the second detector 120b interferes with the light from the second reference optical path 110b and then is detected as the second interference signal by the second detector 120b.

To summarize the above-described configuration, the light amount split ratio S2 of the coupler 130 is set to be smaller in the optical path toward the first detector 120a than in the optical path toward the coupler 104, and the light amount split ratio S4 of the coupler 104 is set to be smaller in the optical path toward the light source 102 than in the optical path toward the second detector 120b.

As a result, it is possible to detect the first interference signal detected by the first detector 120a and the second interference signal detected by the second detector 120b with an appropriate balance. In other words, in a case of the optical path toward the second detector 120b through the coupler 104, the light from the light guiding optical system 150 passes through the plurality of optical splitters (for example, the coupler 130 and the coupler 104), and thus, the number of times of attenuation of the light amount is large. Meanwhile, in a case of the optical path toward the first detector 120a, the light from the light guiding optical system 150 reaches the first detector 120a through the coupler 130, and thus, the number of times of attenuation of the light amount is relatively small.

Here, the light amount split ratio S2 of the coupler 130 is smaller in the optical path toward the first detector 120a than in the optical path toward the coupler 104, and the light amount split ratio S4 of the coupler 104 is smaller in the optical path toward the light source 102 than in the optical path toward the second detector 120b, and accordingly, it is possible to reduce the attenuation of the light amount even when the attenuation of the light amount is performed plural times, and as a result, it is possible to reduce the difference in signal intensity between the first detector 120a and the second detector 120b. Therefore, the difference in signal intensity between the OCT data obtained by the first detector 120a and the OCT data obtained by the second detector 120b is reduced, and appropriate OCT data can be acquired, respectively.

In addition, the light amount split ratio S2 of the coupler 130 and the light amount split ratio S4 of the coupler 104 may be set such that the light amount ratios of the optical path toward the first detector 120a and the optical path toward the second detector 120b are the same as each other. As an example, the light amount split ratio S2 of the coupler 130 may be set such that the optical path toward the first detector 120a:the optical path toward the coupler 104=6:4, and the light amount split ratio S4 of the coupler 102 may be set such that the optical path toward the light source 102:the optical path toward the second detector 120b=1:2.

Not being limited to the description above, with respect to the light amount split ratio S2 of the coupler 130 and the light amount split ratio S4 of the coupler 104, taking into consideration the difference in amount of reflected light at the capturing part of the OCT data detected by the first detector 120a and the second detector 120b, the light amount split ratio may be set. In other words, the reflected light from the cornea of the examinee's eye has a large amount of reflected light, but the light from the crystalline lens and the fundus has a relatively small amount of reflected light. Here, in consideration of the ratio of the amount of the reflected light depending on the capturing part, as a result, the light amount split ratio S2 of the coupler 130 and the light amount split ratio S4 of the coupler 104 may be set such that the signal intensity of the OCT data between the first detector 120a and the second detector 120b are the same.

In addition, in the present example, when the light from the light guiding optical system 150 is guided to the plurality of detectors, the light is divided into the light toward the first detector 120a through one optical splitter (for example, the coupler 130) and the light toward the second detector 120b through the plurality of couplers (for example, the coupler 130 and the coupler 104) because the light from the light guiding optical system 150 is more efficiently guided to each of the detectors. Such an optical disposition is particularly advantageous in a case where the amount of emitted light of the light source 120 is limited and the reflected light from the examinee's eye is weak.

Figure 2:
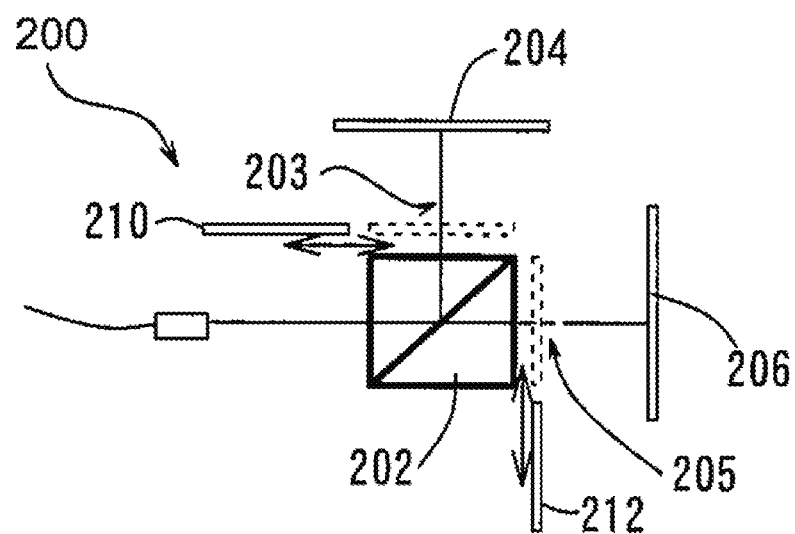
FIG. 2 is a view illustrating an example of an FPN generation optical system according to the embodiment.

FIG. 2 is a view illustrating an example of an FPN generation optical system according to the present example. The FPN generation optical system 200 may include, for example, at least a first optical path 203 including the first optical member 204 and a second optical path 205 including the second optical member 206. Here, between the first optical path 203 and the second optical path 205, by making the optical path length of the first optical path 203 and the optical path length of the second optical path 205 different from each other, the second FPN is generated at a position different from that of the first FPN. For example, by making the optical path length of the second optical path 205 longer than the optical path length of the first optical path 203, the second FPN is generated at a position separated from the zero delay from the first FPN.

The FPN generation optical system 200 may include an optical path splitting member 202 (for example, a beam splitter), and the optical path splitting member 202 may be provided for splitting the optical path on the light source side into the first optical path 203 and the second optical path 205. The first optical member 204 may be disposed in the first optical path 203 split by the optical path splitting member 202, and the second optical member 206 may be disposed in the second optical path split by the optical path splitting member 202.

The first optical path 203 and the second optical path 205 have optical path lengths different from each other. In other words, the optical path length from the branching position of the optical path splitting member 202 to the first optical member 204 is different from the optical path length from the branching position of the optical path splitting member 202 to the second optical member 206. As a result, the first FPN formed by the first optical member 204 and the second FPN formed by the second optical member 206 are formed at different positions in the depth direction on an OCT image. In addition, the distance between the first FPN and the second FPN in the depth direction is caused by the optical path length difference between the first optical path 203 and the second optical path 205.

In addition, the first optical path 203 and the second optical path 205 are set (constructed) to have optical dispersion amounts equal to each other. As a result, based on mapping information (hereinafter, first wavenumber mapping information) of each of the wavenumber components calculated using the first FPN and mapping information (hereinafter, second wavenumber mapping information) of each of the wavenumber components calculated using the second FPN, when obtaining the correction information for correcting the mapping state of each of the wavenumber components by an arithmetic operation, the dispersion component included in each piece of mapping information can be appropriately canceled, and thus, it is possible to obtain the correction information with high accuracy (will be described in detail later). In this case, it is not necessarily required that the dispersion amounts which are equal to each other are strictly the same as each other, and it is only necessary to ensure a certain accuracy and appropriately cancel the dispersion component.

<Polarization Adjustment Mechanism>

In the OCT optical system 100 of the present example, a plurality of polarization adjustment sections may be provided, and for example, in the optical path of the OCT optical system 100, a first polarization adjustment section 300, a second polarization adjustment section 302, and a third polarization adjustment section 304 may be provided (refer to FIG. 1).

The first polarization adjustment section 300 may be disposed in the optical path of the first reference optical path 110a and may be provided for adjusting the polarization state of the reference light through the first reference optical path 110a. The second polarization adjustment section 302 may be disposed in the optical path of the second reference optical path 110b and may be provided for adjusting the polarization state of the reference light through the second reference optical path 110b. The third polarization adjustment section 304 may be disposed in the FPN generation optical system 200 and may be provided for adjusting the polarization state of the light passing through the optical path of the FPN generation optical system 200.

<Acquisition of Depth Information>

When the emitted wavelength is changed by the light source 102, the interference signal light that corresponds thereto is received by the detector 120, and as a result, the light is detected by the detector 120 as a spectrum signal. The control section 70 processes (Fourier analysis) the spectrum signal detected by the detector 120 and obtains the OCT data of the examinee's eye.

The spectrum signal (spectral data) may be rewritten as a function of a wavelength λ, and may be transformed into a function I(k) that is equally spaced with respect to a wavenumber k(=2π/λ). Alternatively, the equally spaced function I(k) with respect to the wavenumber k from the beginning may be acquired (K-CLOCK technology). The arithmetic controller may obtain the OCT data in the depth (Z) region by Fourier transforming the spectrum signal in the wavenumber k space.

Furthermore, the information after the Fourier transform may be expressed as a signal including a real number component and an imaginary number component in a Z space. The control section 70 may obtain the OCT data by obtaining absolute values of the real component and the imaginary component in the signal in the Z space.

In the present example, the control section 70 may process the first interference signal detected by the first detector 120a and obtain the first OCT data, and may process the second interference signal detected by the second detector 120b and obtain the second OCT data. Here, in a case where the first reference optical path 110a and the second reference optical path 120b are set to have optical path lengths different from each other, regarding the first OCT data and the second OCT data, the OCT data in a region of which at least a part thereof is different in the depth direction is acquired. In a case where the first reference optical path 110a and the second reference optical path 120b are set to have the same optical path lengths, regarding the first OCT data and the second OCT data, the OCT data in a region which is the same in the depth direction is acquired.

<Control System>

The control section 70 may include a CPU (processor), a RAM, a ROM, and the like (refer to FIG. 1). For example, the CPU of the control section 70 may control the OCT apparatus. The RAM temporarily stores various types of information. Various programs for controlling the operation of the OCT apparatus, initial values, and the like may be stored in the ROM of the control section 70.

The nonvolatile memory (hereinafter shortened to memory) 72 that serves as a storage section, the display section 75, and the like may be electrically connected to the control section 70. As the memory 72, a non-fugitive storage medium which is capable of holding stored contents even when the supply of power is stopped may be used. For example, as the memory 72, a USB memory or the like which is attachably and detachably mounted to a hard disc drive, a flash ROM, and the OCT apparatus, can be used. In the memory 72, a control program for controlling the acquisition of the OCT data and the capturing of the OCT image may be stored, an arithmetic processing program for combining the OCT image using the FPN and an arithmetic processing program which obtains the correction information for correcting the mapping state of each of the wavenumber components, and the like may be stored. In addition to the OCT image generated from the OCT data, various types of information related to the capturing may be stored in the memory 72. The display section 75 may display the OCT image generated from the OCT data.

<Image Composition Using FPN>

Figure 3:
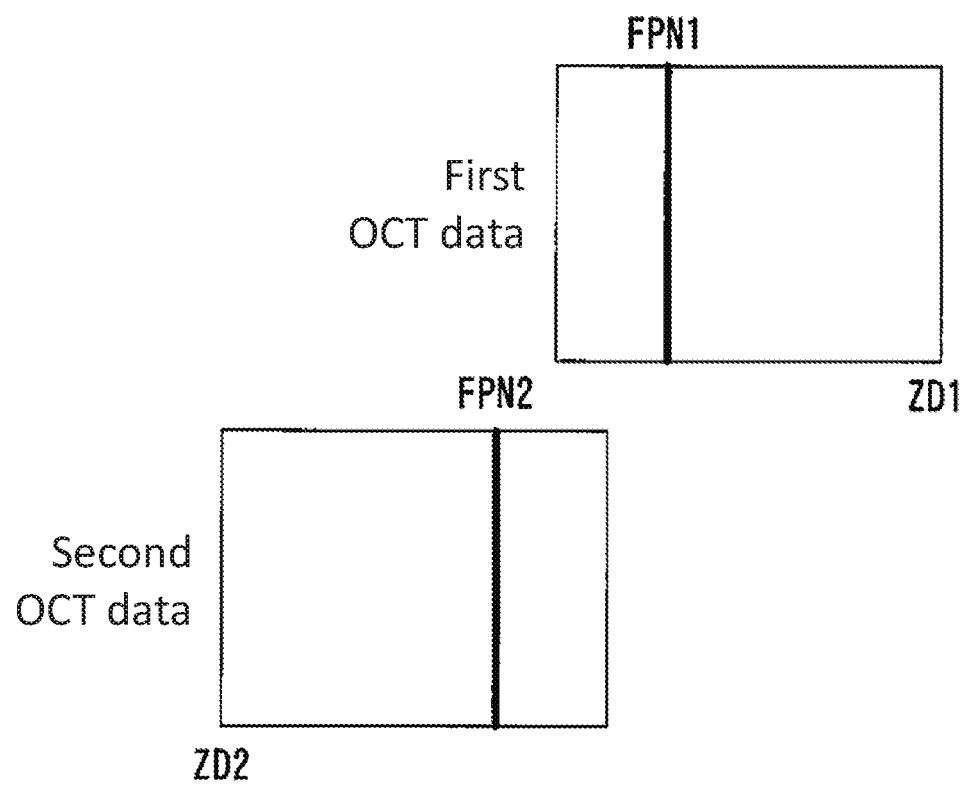
FIG. 3 is a view illustrating an example of data in a case of combining a plurality of OCT data using an FPN signal, and is a view illustrating a state before the combining.
Figure 4:
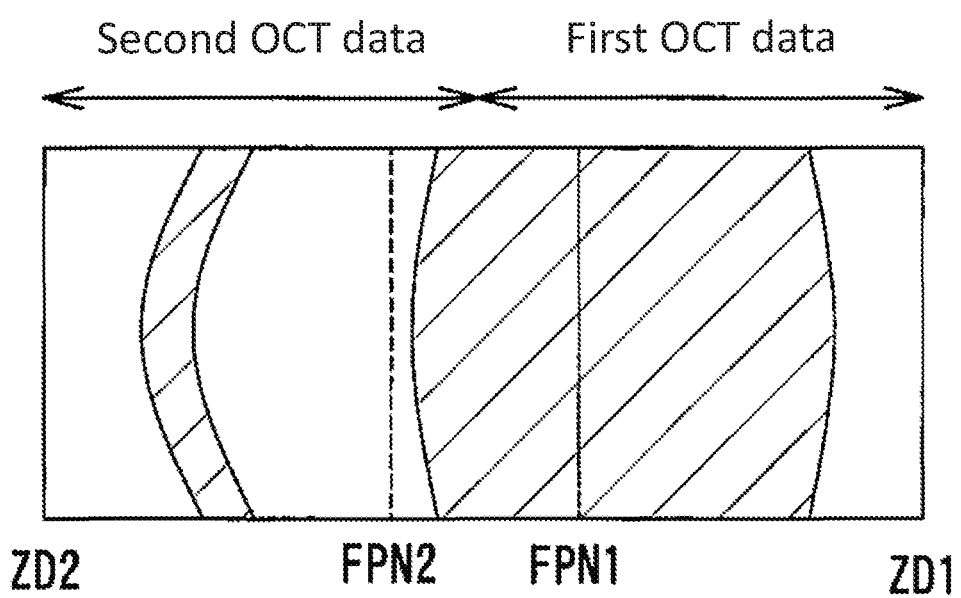
FIG. 4 is a view illustrating an example of data in a case of combining the plurality of OCT data using the FPN signal, and is an image view of a state after the combining.
Figure 5:
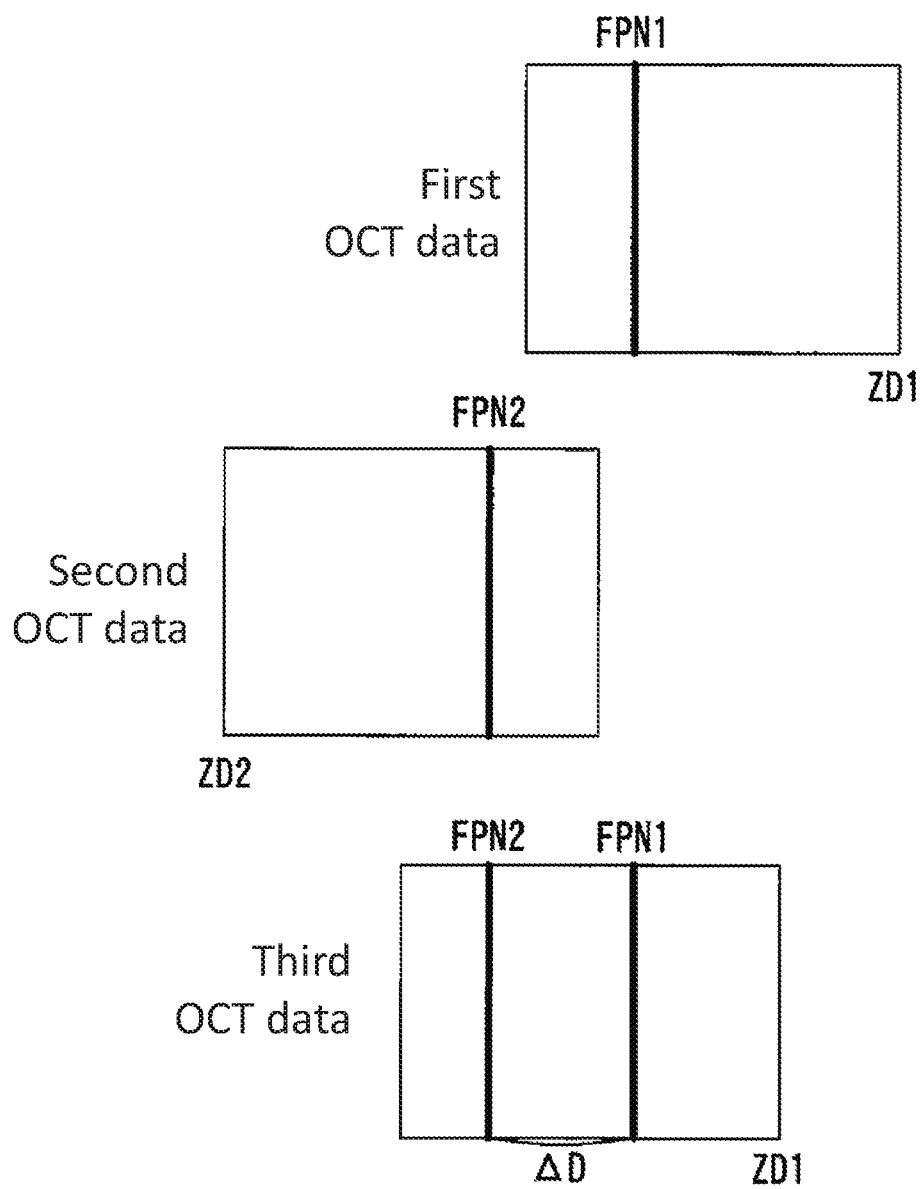
FIG. 5 is a view illustrating a modification example of data in a case of combining the plurality of OCT data using the FPN signal.

In this case, the control section 70 may obtain the combined OCT data, for example, by combining the first OCT data based on the first interference signal and the second OCT data based on the second interference signal, based on the FPN signal detected by the first detector 120a and the FPN signal detected by the second detector 120b (refer to FIGS. 3 to 5). In other words, the FPN signal may be used as a reference signal for combining the plurality of OCT data. Here, in the second OCT data, at least a part of the depth region on the examinee's eye may be different from that in the first OCT data.

As an example, since the disposition position of the optical members (for example, the optical members 204 and 206) for FPN generation is already known in the FPN generation optical system 200, the positional relationship between the first OCT data and the second OCT data may be set using the FPN signal.

According to this, it is possible to appropriately set the positional relationship between the first OCT data and the second OCT data. In addition, in the present example, since the first OCT data is detected by the first detector 120a and the second OCT data is detected by the second detector 120b at the same time, it is possible to reduce the position shift caused by the movement or the like of the examinee's eye.

For example, the FPN generation optical system 200 may be an FPN generation optical system which includes at least the first optical member (for example, first optical member 204) which generates the first FPN and the second optical member (for example, second optical member 206) which generates the second FPN at a position different from that of the first FPN, and generates at least two FPN signals.

The control section 70 may obtain the combined OCT data by combining the first OCT data based on the first interference signal and the second OCT data based on the second interference signal, based on the FPN by the first optical member which is detected by the first detector 120a and the FPN by the second optical member detected by the second detector 120b.

FIGS. 3 and 4 are views illustrating an example of data in a case of combining the plurality of OCT data using the FPN signal, and FIG. 3 is an image view of a state before the combining and FIG. 4 is an image view of a state after the combining. FPN 1 is the FPN signal generated by the first optical member 204 and FPN 2 is the FPN signal generated by the second optical member 206.

In FIG. 3, the FPN 1 is formed in the first OCT data and the FPN 2 is formed in the second OCT data. The first OCT data may be acquired using the first reference optical path 110a and the first detector 110a and the second OCT data may be acquired using the second reference optical path 110b and the second detector 110b.

In a case of setting the positional relationship between the OCT data using the FPN signal, the control section 70 sets the positional relationship between the OCT data, for example, using the FPN 1 included in the first OCT data and the FPN 2 included in the second OCT data. Here, the control section 70 may detect the position of FPN in the depth direction and may combine the plurality of OCT data with reference to the detection position of the FPN (refer to FIG. 4).

Here, since the positional relationship between the first optical member 204 and the second optical member 204 is already known (for example, the optical path length ΔD), in a case of combining the first OCT data and the second OCT, the control section 70 may detect the positions of the FPN 1 and the FPN 2 and may combine the data such that the detected position of the FPN 1 and the detected position of the FPN 2 are separated from each other by the optical path length ΔD separation. In addition, regarding the composition at the overlapping part between the plurality of OCT data, any one piece of OCT data may be used, or an average of both OCT data may be obtained.

The control section 70 may measure the dimensions (for example, anterior chamber depth and eye axial length) of the examinee's eye based on the combined OCT data combined as described above, and may further display the obtained measurement result on the display section 75.

FIG. 5 is a view illustrating a modification example of data in a case of combining the plurality of OCT data using the FPN signal, and the FPN 1 and the FPN 2 are formed in third OCT data. Here, the third OCT data may be acquired using the first reference optical path 110a and the first detector 110a, and by adjusting the optical path length of the first reference optical path 110a, the third OCT data may be acquired.

Here, the control section 70 may set the positional relationship between the first OCT data and the second OCT data using the third OCT data. In this case, the control section 70, for example, may set the positional relationship such that the detection position of the FPN 1 on the first OCT data and the detection position of the FPN 1 on the third OCT data are at the same position in the depth direction, and further, the control section 70, for example, may set the positional relationship such that the detection position of the FPN 2 on the second OCT data and the detection position of the FPN 2 on the third OCT data are the same position in the depth direction. According to this, even when the position of the optical member for FPN generation fluctuates due to secular change, since the actual positional relationship can be used, the positional relationship between the first OCT data and the second OCT data can be more stably set.

In addition, in a case of detecting the position of the FPN in the depth direction, for example, the control section 70 may process the OCT data acquired by the detectors 120a and 120b, and may extract the FPN signal by the optical member (for example, the first optical member 204 or the second optical member 206) for FPN generation. Since the signal intensity of the FPN signal is already known, the control section 70 determines, for example, whether or not each luminance signal of the OCT data exceeds a threshold value set for obtaining the FPN signal, and can extract the FPN signal (reference signal) that corresponds to the optical member for FPN generation. In addition, the FPN 1 and the FPN 2 can be determined using a known disposition.

Figure 6:
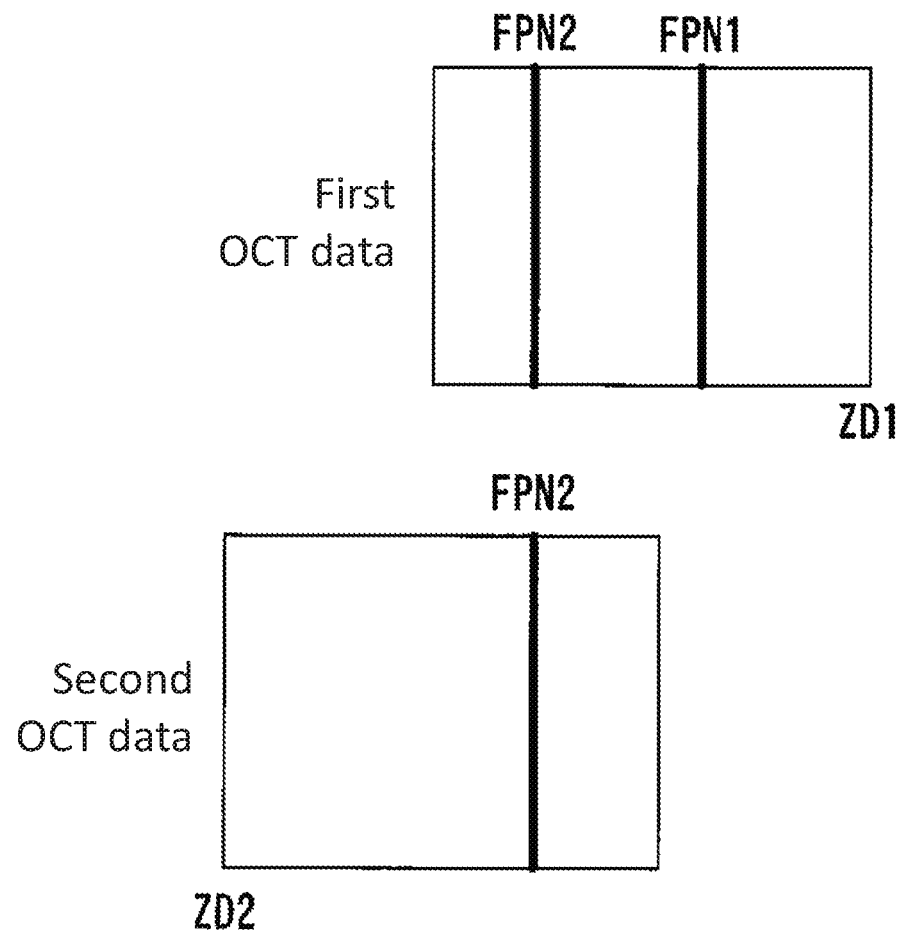
FIG. 6 is a view illustrating a modification example of data in a case of combining the plurality of OCT data using the FPN signal.

In addition, not being limited to the above-described method, the third OCT data in FIG. 5 which is used as the first OCT data, and the second OCT data in FIG. 5 may be combined (refer to FIG. 6). In this case, the FPN 1 and the FPN 2 are formed in the first OCT data and the FPN 2 is formed in the second OCT data. The first OCT data may be acquired using the first reference optical path 110a and the first detector 110a and the second OCT data may be acquired using the second reference optical path 110b and the second detector 110b.

In this case, the control section 70 may detect the position of the FPN 2, may set the positional relationship between the OCT data using the detected position, and may set the positional relationship by matching the FPN 2 of the first OCT data and the FPN 2 of the second OCT data by image processing. In this case, the control section 70 may perform the composition such that the FPN 1 of the first OCT data and the FPN 1 of the second OCT data are identical to each other in the depth direction in the combined OCT data.

In addition, in the present example, regarding the FPN generation optical system 200, the first optical path 203 on which the first optical member 204 is disposed and the second optical path 205 on which the second optical member 206 is disposed are set (constructed) to have the optical dispersion amounts equal to each other. As a result, since a PSF signal by the FPN is similar, for example, even in a case where the quality of the light source is not excellent and the PSF is not unimodal, it is easy to detect the corresponding peak position and the separation can be easily determined.

FIG. 6 can also be considered as an example of image composition using one FPN. Generation of the FPN 1 is not necessarily indispensable. In other words, even in a case where an FPN optical system 200 of the present example includes one optical member for FPN generation, image composition is possible and the configuration of the apparatus can be simplified, but as compared with a case of using the plurality of FPN signals, the capturing range in the depth direction becomes narrow and the number of overlapping regions between different OCT data increases. Meanwhile, in a case of providing a common region, by using the plurality of FPN signals, it is possible to widen the imaging range in the depth direction and to reduce the overlapping region between different OCT data. Otherwise, discontinuous regions may be included between different OCT data. Since the separation between different OCT data can be accurately known, for example, this case is also useful in a case of examining the adjustment function of the eye.

In addition, with respect to the FPN generation optical system 200 according to the present example, since the optical members (for example, the first optical member 204 and the second optical member 206) for FPN generation used for combining the OCT data are arranged in the air, the FPN generated by the surface reflection is used for image composition, and as a result, since it is possible to reduce the signal intensity (SNR) of FPN or the like, it is possible to accurately combine the OCT data using the FPN.

In addition, the timing of obtaining the FPN signal may be, for example, the time when turning on the power or may be every time the examinee is changed. Further, the timing of obtaining the FPN signal may be the time of optimization control for optimizing the capturing conditions in the OCT optical system. Naturally, not being limited thereto, the timing of obtaining the FPN signal may be any time. For example, in the control section, the OCT data including the FPN signal is acquired in advance, and the composition of the OCT data acquired later, correction of the mapping state, polarization adjustment and the like may be performed using the FPN signal acquired in advance.

<Light Shielding Member>

In addition, by disposing a light shielding member or a light reducing member in the optical path of the FPN generation optical system 200, the FPN signal of the OCT data used for observing or capturing the examinee's eye may be reduced. In this case, the FPN signal on the OCT data may be reduced as at least one of the first optical path and the second optical path is shielded or dimmed. These are effective in a case of obtaining the OCT data used for diagnosis, observation and the like. In addition, not being limited thereto, the FPN signal included in the OCT data may be removed by signal processing.

For example, in the optical path of the FPN generation optical system 200, the first light shielding member 210 for shielding the first optical path and a second light shielding member 212 for shielding the second optical path may be disposed to be insertable into each of the optical paths.

<Wavenumber Mapping Correction>

Figure 7:
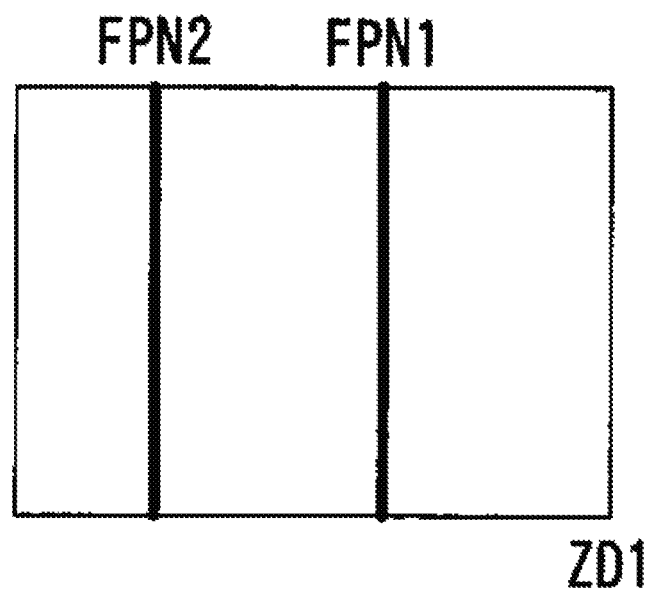
FIG. 7 is a view illustrating an example of the OCT data used for wavenumber mapping correction.

FIG. 7 is a view illustrating an example of the OCT data according to the present example in which the first FPN signal and the second FPN signal are simultaneously formed on the OCT data. In addition, the OCT image of the examinee's eye may be included on the OCT data.

In this case, the control section 70 may process the signal including both the first FPN and the second FPN at the same time, and may acquire correction information for correcting the mapping state of each of the wavenumber components. In other words, the control section 70 may be used, for example, as an arithmetic processor for obtaining the correction information. In addition, the correction information may also be acquired by a processor different from the control section that drives the OCT optical system. Further, the control section 70 may generate the correction information using a phase difference information of at least two FPN signals accompanying sweeping of the wavelength by the light source 102, for example, during capturing or before capturing the OCT image.

More specifically, the control section 70 may correct the mapping state (wavenumber sampling mapping) of each wavelength component (wavenumber components) with respect to a sampling point p based on at least two FPN signals generated by the FPN generation optical system 200.

For example, by analyzing the intensity level of the FPN, the control section 70 may obtain $\phi(k)$ in the spectrum signal at the position that corresponds to the FPN. $\phi(k)$ indicates a change in phase $\phi$ of the spectrum signal in accordance with the sweep wavelength (wavenumber). $\phi(k)$ may be expressed by a function that has the horizontal axis indicating the wavenumber k and the vertical axis indicating the phase $\phi$. Polynomial fitting may be performed on $\phi(k)$ in the wavenumber k region with large signal intensity (amplitude), and $\phi(k)$ in the wavenumber k region with small signal intensity may be obtained by extrapolation or interpolation. For example, $\phi(k)$ may be obtained from ArcTangent (arctangent) of the ratio of the real part RealF to the imaginary part ImagF of the Fourier transform value (intensity value) F at the depth position that corresponds to FPN. Here, the arctangent of the ratio between the real part and the imaginary part of the Fourier transform value is calculated by ArcTangent processing, and $\phi(k)$ is obtained.

Figure 8:
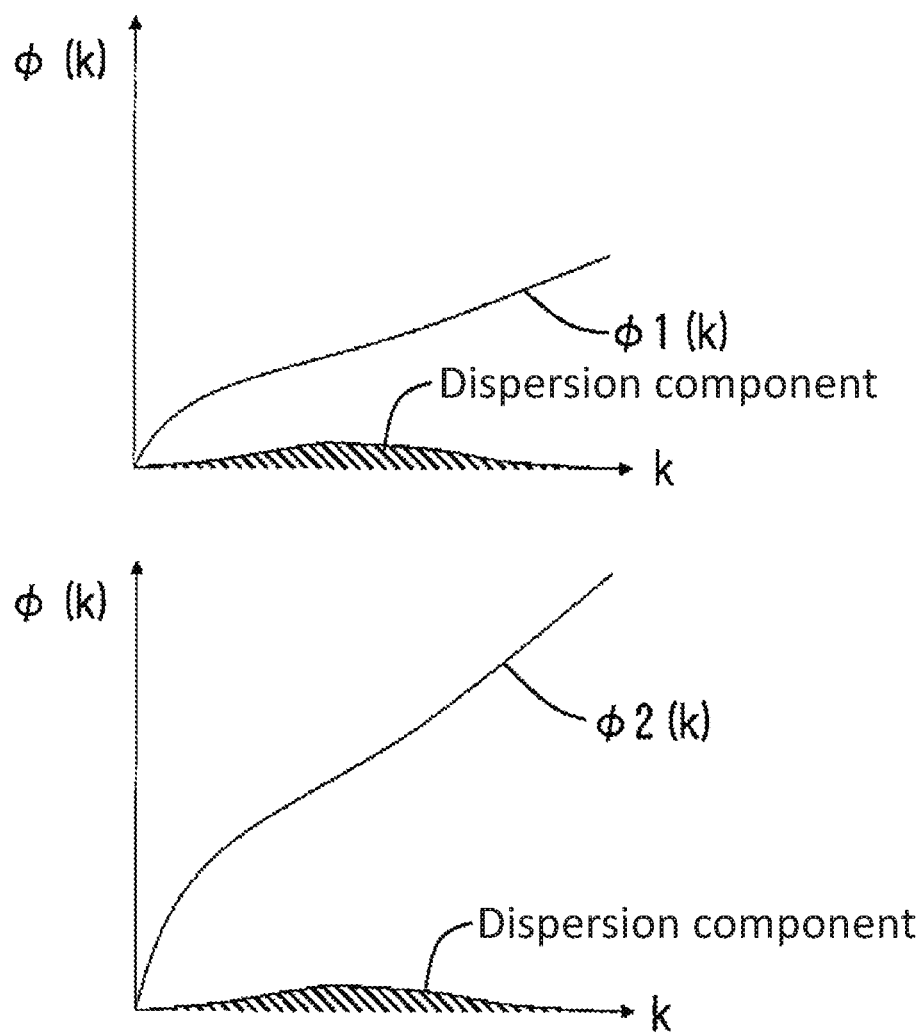
FIG. 8 is a view illustrating an example of wavenumber mapping information obtained by processing FPN.

In a case where at least two FPN signals are simultaneously obtained, the control section 70 may process the first FPN and obtain first wavenumber mapping information $\phi 1(k)$, and may process the second FPN and obtain second wavenumber mapping Information $\phi 2(k)$ (refer to FIG. 8). In this case, each wavenumber mapping information may be obtained as phase information of each of the wavenumber components.

Furthermore, the control section 70 may obtain the difference information $\Delta\phi(k)$ between the first wavenumber mapping information $\phi 1(k)$ and the second wavenumber mapping information $\phi 2(k)$ (refer to FIG. 5). In addition, the wavenumber mapping information may be obtained as the phase difference information of each of the wavenumber components. In a case of obtaining the difference information $\Delta\phi(k)$, the difference information may be obtained with $\Delta\phi(k)=\phi 2(k)-\phi 1(k)$ since the phase advance of the second FPN is earlier. In addition, by obtaining the difference information, the dispersion component included in each wavenumber mapping information can be canceled. In this case, as described above, it is preferable that the dispersion amount between the first optical path 203 and the second optical path 205 be equal to each other.

Here, assuming that the optical distance (optical path length difference) between the first FPN and the second FPN is $\Delta Z$, and when the difference information $\Delta\phi(k)$ is ideal, a straight line as illustrated in the following equation (1) is achieved.

$$\Delta\phi(k)=\Delta Zk \qquad (1)$$

Here, $\Delta Z$ is obtained as follows. An interference component can be generalized as exp(ikz), and k and z have a relationship of $kz=2\pi$. From this point of view, z can be expressed as the following equation (2), where N is the number of sampling points and kmax and kmin are the maximum and minimum values of the k value detected at each sampling point.

$$z = \frac{2\pi \cdot i}{k_{max} - k_{min}} \qquad (2)$$

In addition, i=0, 1, 2, . . . , N/2 is achieved.

Here, assuming that the interference signal that corresponds to $\Delta Z$ is detected at the sampling point that corresponds to i($\Delta Z$), $\Delta Z$ can be expressed by the following expression (3).

$$\Delta Z = \frac{2\pi \cdot i(\Delta Z)}{k_{max} - k_{min}} \qquad (3)$$

Since $\Delta\phi(k)$ is supposed to ideally be a straight line with slope $\Delta Z$ and intercept 0, when second and third order nonlinear terms are σ, k is corrected to the following equation (4).

$$k' = k + \frac{\sigma}{\Delta Z} \qquad (4)$$

After this, the corrected wavelength λ' is determined as λ'=2π/k'. Here, σ is the nonlinear term $\sigma=b_2 k^2+b_3 k^3$ when expanded to the following equation (5).

$$\phi(k) = \sum_{i=0}^{3} b_i k^i \qquad (5)$$

In addition, in the above-described example, the nonlinear term is third order, but not being limited thereto, and more nonlinear terms may be adopted. For example, approximately ninth order may also be adopted. Otherwise, other fitting methods (chirped sine wave fitting method) may be used.

Figure 9:
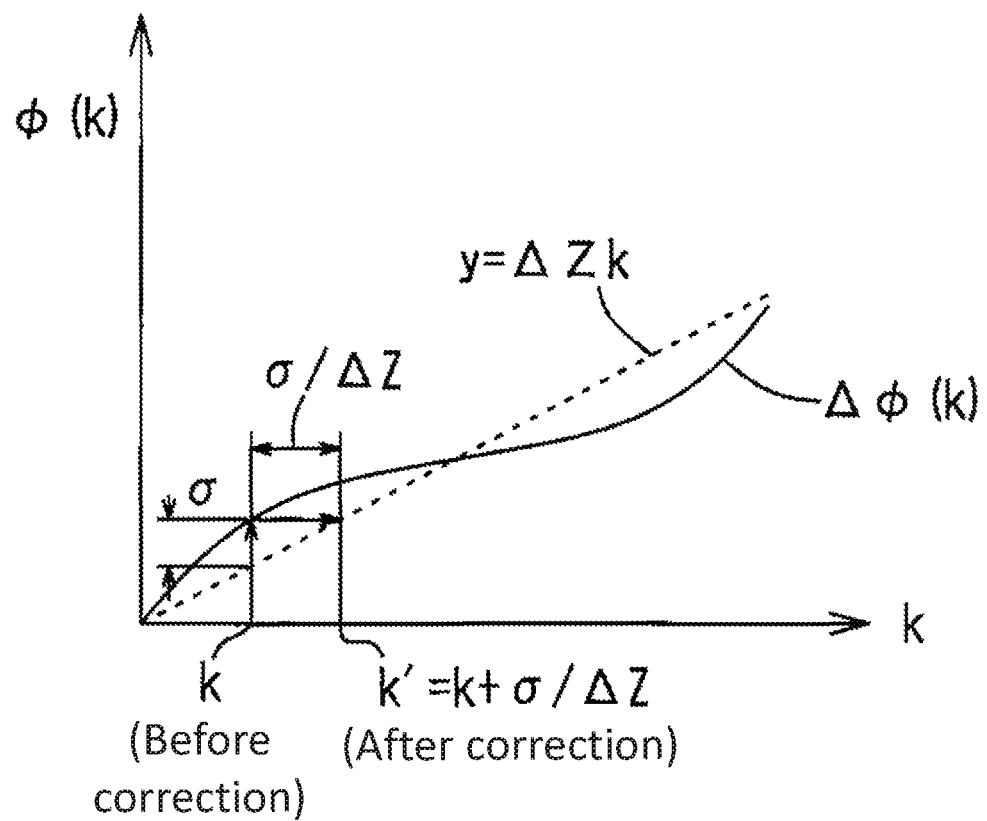
FIG. 9 is a view illustrating an example for correcting a mapping state in a case of obtaining difference information $\Delta\phi(k)$ between first wavenumber mapping information $\phi1(k)$ and second wavenumber mapping information $\phi2(k)$.

In addition, FIG. 9 is a view schematically illustrating the mapping of the spectrum signal to be corrected by performing the correction calculation. In addition, when the corrected values of $\Delta\phi(kmin)$ and $\Delta\phi(kmax)$ are within a predetermined allowable range (for example, approximately $1E^{-5}$) from the ideal values z(peak)·kmin, z(peak)·kmax, convergence is determined, and when the condition is not satisfied, the same calculation is repeated using the corrected λ' described above.

As described above, the control section 70 may obtain the correction information from at least two FPN signals generated using the FPN generation optical system 200 by the arithmetic operation, and may store the obtained correction information in the memory 72. Accordingly, the correspondence relationship between each wavelength component detected by the detector 120 and each sampling point can be more accurately obtained. The obtained correction information may be used for acquiring OCT data. In addition, the method of obtaining ϕ(k) from the FPN and the method of obtaining the wavenumber mapping information, reference should be made to JP-A-2013-156229, JP-A-2015-68775, and the like.

In addition, in the description above, a case where the wavenumber mapping information is corrected in the SS-OCT is described, but the invention is not limited thereto, and the present example can also be applied in a case where the wavenumber mapping information is corrected in the SD-OCT. In this case, for example, the control section 70 may correct the mapping state of each wavelength (wavenumber) with respect to each sampling point of spectrometer based on at least two FPN signals generated by the FPN generation optical system 200. In this case, reference may be made to JP-A-2010-220774.

In addition, refer to JP-A-2017-017156 for the wavenumber mapping correction according to the present example.

In addition, the timing of obtaining the correction information for correcting the mapping state of each of the wavenumber components, for example, may be the time when turning on the power or may be every time the examinee is changed. Further, the timing of acquiring the FPN signal may be the time of optimization control for optimizing the capturing conditions in the OCT optical system. Naturally, not being limited thereto, the timing of obtaining the FPN signal may be any time. In addition, after correcting the mapping state, the FPN on the OCT image may be removed by noise removal processing.

In addition, in the description above, the FPN generation optical system is provided at a position branched from the measurement optical path. However, the invention is not limited thereto as long as the FPN generation optical system is in the optical path of the OCT optical system. For example, the FPN generation optical system may be disposed at a position branched from the reference optical path of the OCT optical system. In this case, for example, the FPN signal due to interference between the light from the FPN generation optical system and the reference light (or the measurement light) may be obtained. Further, for example, the FPN generation optical system may be disposed at a position branched from the optical path after the measurement optical path and the reference optical path join together. In this case, for example, the FPN signal due to the interference between the interference light directly toward the optical path of the interference light and the interference light from the FPN generation optical system provided at a position branched from the optical path of the interference light may be obtained, and may be detected by the detector 120. In addition, in a case where the detector 120 includes the first detector 120*a* and the second detector 120*b*, the FPN generation optical system is disposed before being split into the optical paths of each of the detectors, and accordingly, similar FPN signals may be detected by each of the detectors.

<Example Applied to Examinee's Eye>

The present apparatus may be an ophthalmic OCT apparatus for acquiring the OCT data of the examinee's eye. For example, the ophthalmic OCT apparatus may be configured to be capable of acquiring the OCT data of the fundus and the OCT data of the anterior ocular segment including the cornea and the crystalline lens, and further, may be configured to be capable of measuring the eye axial length based on the OCT data of the cornea and the fundus.

For example, the ophthalmic OCT apparatus may be configured to switch the optical disposition of the OCT optical system 100 corresponding to the automatic or manual mode switching signal. Hereinafter, an example of a case where mode switching of a fundus capturing mode, an anterior ocular segment capturing mode, and an eye axial length measuring mode will be described.

<Fundus Capturing Mode>

In a case where the fundus capturing mode is set, the control section 70 may control the light guiding optical system 150 and switch to the optical disposition for obtaining the OCT data of the fundus. In this case, for example, the control section 70 may switch the optical disposition of the light guiding optical system 150 such that the pivot point of the measurement light is formed on the examinee's eye pupil and a focus position of the measurement light is formed on the fundus. In addition, for example, refer to JP-A-2016-209577 for the configuration related to the switching of the optical disposition of the light guiding optical system 150.

In a case where the fundus capturing mode is set, the control section 70 may adjust the optical path length of at least one of the measurement light and the reference light, and set an acquisition region of the OCT data to fundus. In this case, for example, the control section 70 may adjust the optical path length difference between the measurement light and the reference light such that the optical path length of the reference light that has passed through at least one of the plurality of reference optical paths is identical to the optical path length of the measurement light that has passed through the fundus. In addition, in a case where the optical path length difference is adjusted, the adjustment may be performed such that the OCT data is acquired in a state where the retina is formed on the father inner side than the zero delay position, or the adjustment may be performed such that the OCT data is acquired in a state where the choroid layer is formed further on the farther front side than the zero delay position.

In the present example, for example, the optical path length of the measurement light may be adjusted as the optical member disposed in the measurement optical path is moved such that the optical path length of the measurement light from the fundus is identical to the reference light from the first reference optical path 110*a*. According to this, at least the OCT data of the fundus is included in the first OCT data obtained based on the output signal from the first detector 110*a*.

Figure 10:
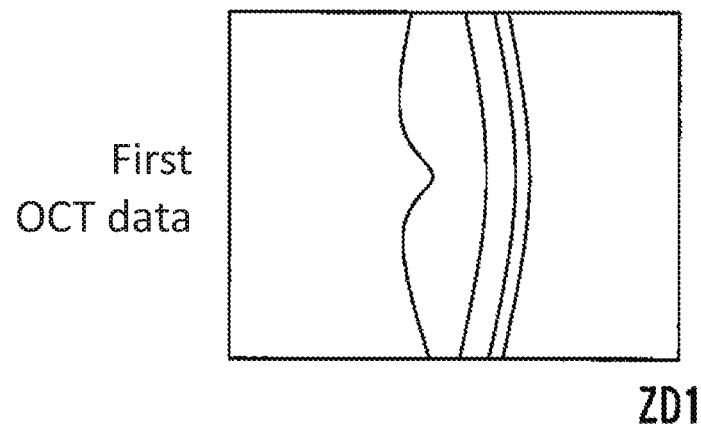
FIG. 10 is a view illustrating an example of the OCT data acquired in a fundus capturing mode.
Figure 10:
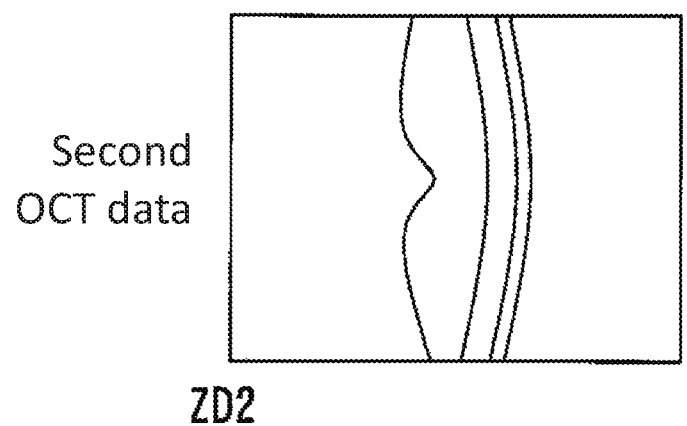

FIG. 10 is a view illustrating an example of the OCT data acquired in the fundus capturing mode. The control section 70 may move the optical member 112 and adjust the optical path length of the second reference optical path 110*b* so as to have the optical path length which is the same as that of the first reference optical path 110*a*. As a result, the first OCT data based on the first detector 110*a* and the second OCT data based on the second detector 110*b* are the same region of the fundus. In this case, the control section 70 may obtain the combined OCT data (for example, an added averaged image and a super resolution image) based on the first OCT data and the second OCT data. According to this, for a short period of time, excellent OCT data of the fundus related to a predetermined capturing region can be obtained.

<Eye Axial Length Measuring Mode>

In a case where the eye axial length measuring mode is set, the control section 70 may control the light guiding optical system 150 and switch to the optical disposition which is the same as that of the above-described fundus capturing mode. In this case, for example, the control section 70 may switch the optical disposition of the light guiding optical system 150 such that the pivot point of the measurement light is formed on the pupil and the focus position of the measurement light is formed on the fundus. According to this, in the OCT data obtained in the eye axial length measurement, it is possible to acquire morphological information of the fundus in detail (for example, information on the vicinity of the macula), and as a result, it is possible to measure the eye axial length of the examinee's eye with high accuracy.

In a case where the eye axial length measuring mode is set, the control section 70 may adjust the optical path length of at least one of the measurement light and the reference light, may set the acquisition region of the OCT data by one of the first detector 120a and the second detector 120b to the fundus, and may set the acquisition region of the OCT data by the other of the first detector 120a and the second detector 120b to the cornea.

Figure 11:
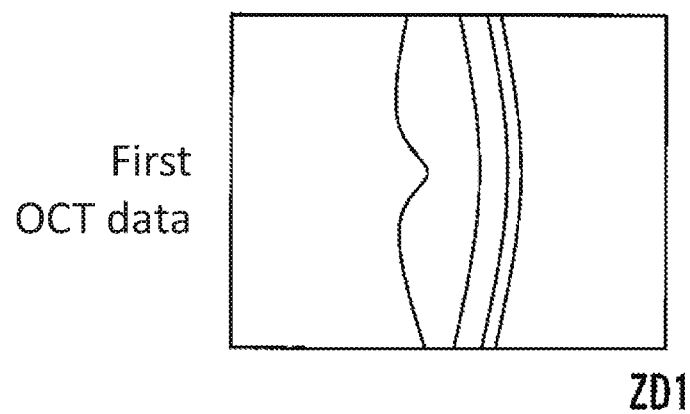
FIG. 11 is a view illustrating an example of the OCT data acquired in an eye axial length capturing mode.
Figure 11:
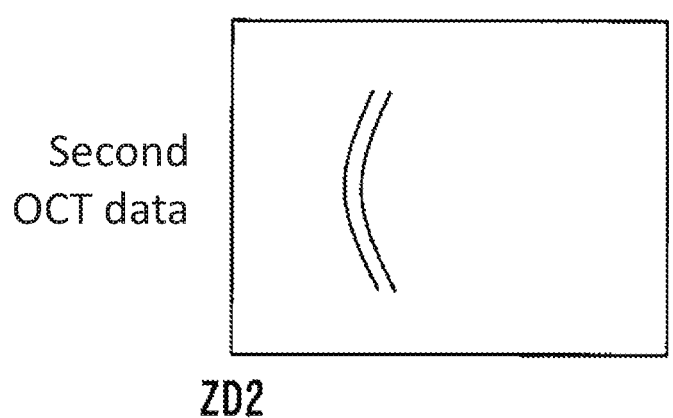

FIG. 11 is a view illustrating an example of the OCT data acquired in an eye axial length capturing mode. In the present example, for example, the optical path length of the measurement light may be adjusted as the optical member disposed in the measurement optical path is moved such that the optical path length of the measurement light from the fundus is identical to the reference light from the first reference optical path 110a. According to this, at least the OCT data of the fundus is included in the first OCT data obtained based on the output signal from the first detector 110a.

In a state where the position of the optical member disposed in the measurement optical path is adjusted such that the OCT data of the fundus is included in the first OCT data, for example, the control section 70 may adjust the optical path length of the reference light of the second reference optical path 110b as the optical member 112 disposed in the second reference optical path 110b is moved such that the optical path length of the measurement light from the cornea and the reference light from the second reference optical path 110b are identical to each other. According to this, the OCT data of the cornea is included in the second OCT data obtained based on the output signal from the second detector 110b.

When the OCT data of the fundus and the OCT data of the cornea are acquired, the control section 70 may detect the retina position based on the OCT data of the fundus and detect the cornea position based on the OCT data of the cornea. The control section 70 may measure the eye axial length using the detection result of the retina position, the detection result of the cornea position, and the optical path length difference between the first reference optical path 110a and the second reference optical path 110b.

In this case, for example, the optical path length difference between the first reference optical path 110a and the second reference optical path 110b may be obtained by a driving position of the driving section for moving the optical member 112, or may be detected based on the position of the optical member 112. In addition, in a case where the optical path length difference between the first reference optical path 110a and the second reference optical path 110b is fixed, a known optical path length difference may be used. In addition, the invention is not limited thereto, and in the FPN generation optical system 200, a configuration may be adopted in which the FPN generation optical member for generating the FPN signal that corresponds to the cornea and the FPN generation optical member for generating the FPN signal that corresponds to fundus are provided, and the optical path length difference may be acquired using the known position of the optical member. In this case, three or more FPN generation optical members may be used corresponding to the optical path length difference.

<Anterior Ocular Segment Capturing Mode>

In a case where the anterior ocular segment capturing mode is set, the control section 70 may control the light guiding optical system 150 and switch to the optical disposition for obtaining the OCT data of the anterior ocular segment including the cornea and the crystalline lens. In this case, the control section 70 may switch the optical disposition of the light guiding optical system 150 such that the pivot point of the measurement light is formed further on the apparatus side than examinee's eye pupil and the focus position of the measurement light is formed on the anterior ocular segment. In addition, for example, refer to JP-A-2016-209577 for the configuration related to the switching of the optical disposition of the light guiding optical system 150.

In a case where the anterior ocular segment capturing mode is set, the control section 70 may adjust the optical path length of at least one of the measurement light and the reference light, may set the acquisition region of the OCT data by one of the first detector 120a and the second detector 120b to the crystalline lens, and may set the acquisition region of the OCT data by the other of the first detector 120a and the second detector 120b to the cornea. Here, the OCT data acquired by the first detector 120a and the OCT data acquired by the second detector 120b differ in at least a part of the acquisition region on the examinee's eye in the depth direction. According to this, the OCT data including a cornea region and the OCT data including a crystalline lens region may be acquired. In this case, the OCT data including the cornea region includes at least the cornea and the crystalline lens front surface, and the OCT data including the crystalline lens region may include at least the crystalline lens rear surface. In other words, the OCT data of a front region in an anterior ocular segment region and the OCT data of a rear region in the anterior ocular segment region may be separately acquired.

In addition, for example, the control section 70 may combine the OCT data including the crystalline lens region and the OCT data including the cornea region. In this case, the composition processing using the above-described FPN signal may be used, and the optical path length of the FPN generation optical system 200 may be set such that the optical path length of the measurement light from the cornea and the crystalline lens and the optical path length of the measurement light that has passed through the FPN generation optical system 200 are identical to each other. In other words, in a state where the optical path length difference between the measurement light of the light guiding optical system 150 and the reference light is set such that the OCT data including the cornea region and the OCT data including the crystalline lens region can be acquired, the FPN generation optical system 200 may be set such that the FPN signal is included in each piece of the OCT data.

In addition, in a case where the optical path length difference is adjusted, the adjustment may be performed such that the OCT data including the cornea region is acquired in a state where the cornea front surface is formed on the farther inner side than the zero delay position, or the adjustment may be performed such that the OCT data including the crystalline lens region is acquired in a state where the crystalline lens rear surface is formed on the farther front side than the zero delay position. Accordingly, it is possible to avoid the influence of the mirror image at the time of image composition. Further, between the first OCT data and the second OCT data, the optical path length difference between the first reference optical path 110a and the second reference optical path 110b may be set such that some parts of the acquisition region on the examinee's eye overlap each other in the depth direction. According to this, it is possible to smoothly perform linking in image composition.

Figure 12:
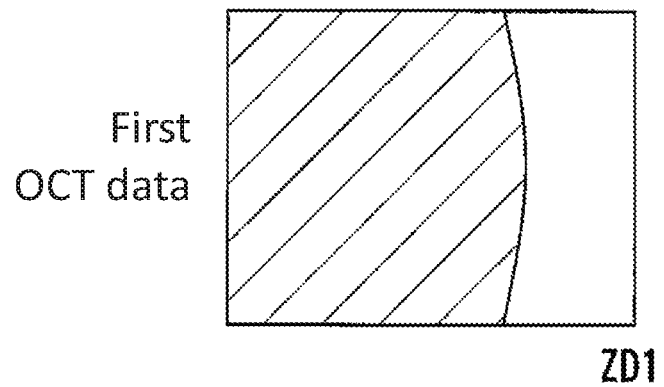
FIG. 12 is a view illustrating an example of the OCT data acquired in an anterior ocular segment capturing mode.
Figure 12:
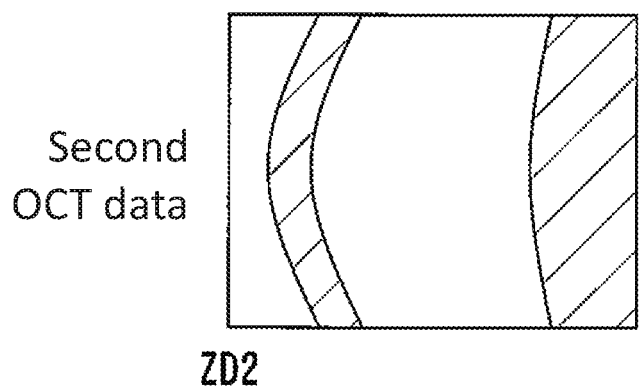

FIG. 12 is a view illustrating an example of the OCT data acquired in the anterior ocular segment capturing mode. In the present example, for example, the optical path length of the measurement light may be adjusted as the optical member disposed in the measurement optical path is moved such that the optical path length of the measurement light from the crystalline lens is identical to the reference light from the first reference optical path 110a. According to this, at least the OCT data of the crystalline lens region is included in the first OCT data obtained based on the output signal from the first detector 110a.

In a state where the position of the optical member disposed in the measurement optical path is adjusted such that the OCT data of the crystalline lens is included in the first OCT data, for example, the control section 70 may adjust the optical path length of the reference light of the second reference optical path 110b as the optical member 112 disposed in the second reference optical path 110b is moved such that the optical path length of the measurement light from the cornea and the reference light of the second reference optical path 110b are identical to each other. According to this, the OCT data of the cornea is included in the second OCT data obtained based on the output signal from the second detector 110b.

When the OCT data of the crystalline lens and the OCT data of the cornea are acquired, for example, the control section 70 may combine the OCT data of the crystalline lens and the OCT data of the cornea and acquire the combined OCT data. Furthermore, the control section 70 may detect the cornea position, the crystalline lens position, and the like based on the combined OCT data and measure the anterior chamber depth, crystalline lens thickness, and the like of the examinee's eye.

<Correction of OCT Data Using FPN Signal Included in Other Piece of OCT Data>

The control section 70 may acquire the OCT data including the FPN signal in one of the first OCT data and the second OCT data, and may acquire the OCT data which does not include the FPN signal in the other of the first OCT data and the second OCT data. In addition, the control section 70 may obtain the wavenumber mapping information based on the FPN signal in the OCT data including the FPN signal, and may correct the OCT data which does not include the FPN signal. According to the configuration, in a case of using a plurality of detectors, it is not always necessary to provide the FPN generation optical system corresponding to each of the detectors. In this case, the control section 70 may correct the OCT data which does not include the FPN signal in real time, and according to this, it is possible to perform the correction of the OCT data with higher accuracy.

In this case, for example, the control section 70 may adjust the optical path length of at least one of the measurement light and the reference light, and may set the acquisition region of the OCT data by one of the first detector 120a and the second detector 120b to a predetermined capturing part (for example, the fundus, the cornea, and the crystalline lens). Further, the control section 70 sets the acquisition region of the OCT data by the other of the first detector 120a and the second detector 120b in the optical member (for example, the optical member 204 and the optical member 206) of the FPN generation optical system 200.

Figure 13:
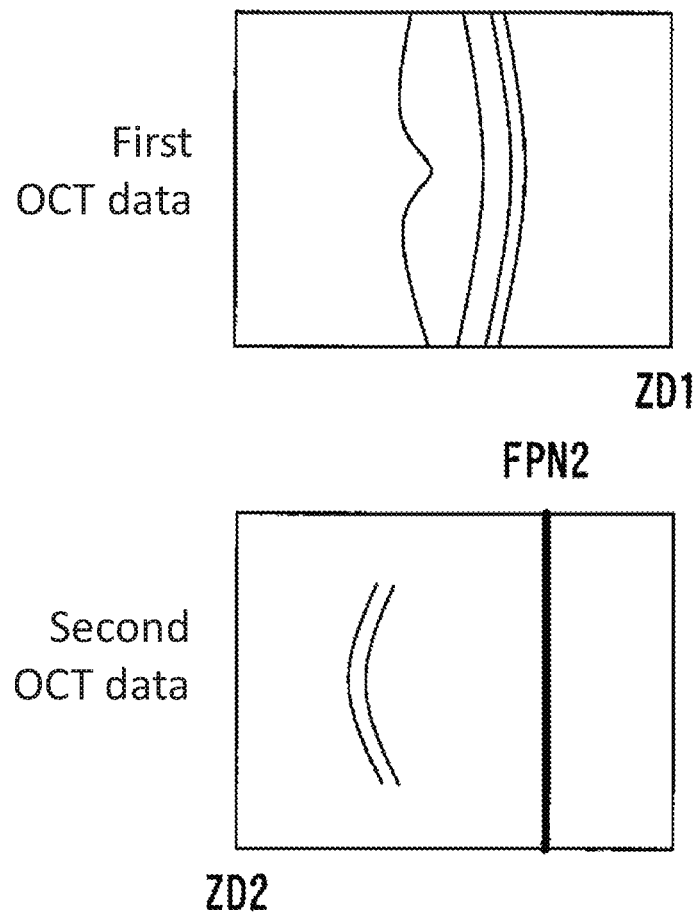
FIG. 13 is a view illustrating an example in a case of applying real time correction in the fundus capturing mode.

FIG. 13 is a view illustrating an example in a case of applying real time correction in the fundus capturing mode. For example, the control section 70 may adjust the optical path length of at least one of the measurement light and the reference light, and may set the acquisition region of the OCT data by one of the first detector 120a and the second detector 120b to the fundus (refer to the above-described fundus capturing mode).

Further, the control section 70 sets the acquisition region of the OCT data by the other of the first detector 120a and the second detector 120b in the optical member (for example, the optical member 204 and the optical member 206) of the FPN generation optical system 200. In this case, the optical path length of the FPN generation optical system 200 is set to a length different from the optical path length of the measurement light that has reached the detector 120a via the fundus. For example, the control section 70 may adjust the optical path length difference between the measurement light and the reference light such that the optical path length of the reference light that has passed through at least one of the plurality of reference optical paths is identical to the optical path length of the measurement light that has passed through the FPN generation optical system 200.

In the present example, for example, the optical path length of the measurement light may be adjusted as the optical member disposed in the measurement optical path is moved such that the optical path length of the measurement light from the fundus is identical to the reference light from the first reference optical path 110a. According to this, at least the OCT data of the fundus is included in the first OCT data obtained based on the output signal from the first detector 110a.

In addition, in the control section 70, in a state where the position of the optical member disposed in the measurement optical path is adjusted such that the OCT data of the fundus is included in the first OCT data, for example, the control section 70 may adjust the optical path length of the reference light of the second reference optical path 110b as the optical member 112 disposed in the second reference optical path 110b is moved such that the optical path length of the measurement light from the optical member of the FPN generation optical system 200 and the reference light from the second reference optical path 110b are identical to each other. According to this, the OCT data including the FPN signal is included in the second OCT data obtained based on the output signal from the second detector 110b. In this case, as a result, in addition to the FPN signal, signals such as the cornea, the crystalline lens and the like may be included.

In addition, in the description above, the application example in the fundus capturing mode is described, but the invention is not limited thereto, and the above-described configuration may be applied in other capturing modes.

In addition, in the description above, in a case where the OCT data including the FPN signal (for example, only the FPN signal) is acquired in one of the first OCT data and the second OCT data, and the OCT data of the examinee's eye which does not include the FPN signal is acquired in the other of the first OCT data and the second OCT data, the invention is not limited to the above-described optical path length adjustment, and the light shielding member may be used. For example, the control section 70 may obtain the first OCT data which does not include the FPN (for example, the FPN 1) by disposing the light shielding member 210 in the first optical path. In this case, since the light shielding member 212 is removed from the second optical path, the second OCT data including the FPN (for example, the FPN 2) is obtained. In addition, in a case where only the FPN signal is obtained, the correction using the FPN signal can be performed with high accuracy.

<Polarization Adjustment>

The control section 70 may control the polarization adjustment section (for example, the first polarization adjustment section 300, the second polarization adjustment section 302, and the third polarization adjustment section 304), and may adjust the polarization state at the time of obtaining the OCT data. In addition, the timing of adjusting the polarization state may be, for example, the time when turning on the power or may be every time the examinee is changed. Further, the timing of obtaining the FPN signal may be the time of optimization control for optimizing the capturing conditions in the OCT optical system.

Figure 14:
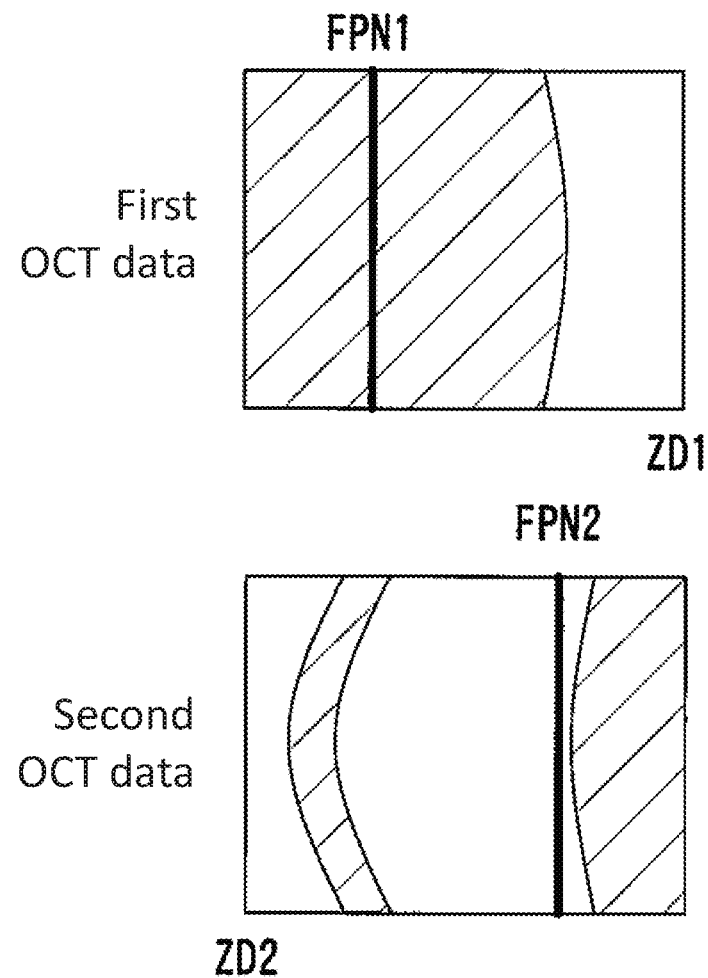
FIG. 14 is a view illustrating an example of the OCT data in a case of performing polarization adjustment in the anterior ocular segment capturing mode.

Hereinafter, adjustment of the polarization state in the anterior ocular segment capturing mode will be described as an example. FIG. 14 is a view illustrating an example of the OCT data in a case of performing the polarization adjustment in the anterior ocular segment capturing mode. First, the control section 70 controls the second polarization adjustment section 302 and adjusts the polarization state such that the signal intensity of a cornea image in the second OCT data becomes maximum. According to this, the cornea image in the second OCT data is acquired with excellent signal intensity.

Figure 15:
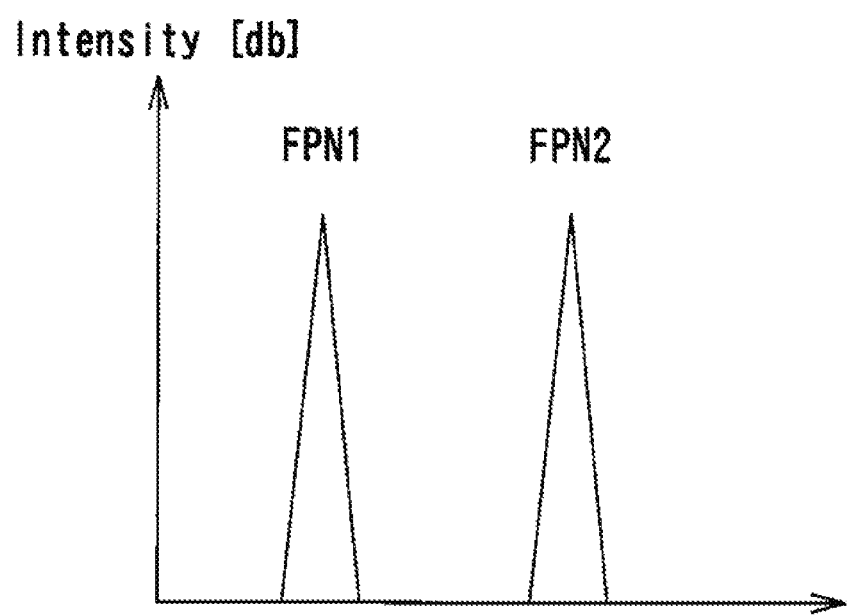
FIG. 15 is a view illustrating an example of signal intensity of the FPN.

FIG. 15 is a view illustrating an example of the signal intensity of the FPN. Next, the control section 70 controls the third polarization adjustment section 304 and adjusts the polarization state such that the signal intensity of the FPN signal in the second OCT data becomes maximum. According to this, the FPN signal in the second OCT data is acquired with excellent signal intensity. As a result, the cornea image and the FPN signal in the second OCT data are acquired with excellent signal intensity.

Next, the control section 70 controls the first polarization adjustment section 300 and adjusts the polarization state such that the signal intensity ratio of the FPN signal in the second OCT data to the FPN signal in the first OCT data becomes a predetermined signal intensity (for example, a state where the signal intensity ratios of the signals are equal to each other). According to this, the FPN signal in the first OCT data is acquired with excellent signal intensity, and the crystalline lens image in the first OCT data is acquired with excellent signal intensity.

According to the above-described control, it is possible to adjust the balance of the signal intensity between the first OCT data and the second OCT data. Furthermore, by using the signal intensity ratio of the FPN signal in the second OCT data to the FPN signal in the first OCT data in the adjustment of the polarization state related to the OCT data including the crystalline lens, the polarization state is adjusted with higher accuracy than a case where the polarization state is adjusted using the crystalline lens image. In other words, there is a possibility that the crystalline lens image in this case is limited only to the information on the crystalline lens rear surface, and since the information amount as the image is relatively small, there is a possibility that the accuracy as the signal evaluation value is low. As a result, there is a case where it is not possible to adjust to excellent polarization state. Meanwhile, by using the FPN signal, it is possible to ensure stable signal intensity, and thus, it is possible to ensure the accuracy as the signal evaluation value, and to excellently adjust the polarization state.

In addition, in a case of the polarization state optimized only for the information on the crystalline lens rear surface, polarization mismatch detected between the first OCT data and the second OCT data occurs, and accordingly, a gap of the intensity signal is generated in the region where both data are connected to each other. This is remarkable, for example, in a case where the crystalline lens is at a gap position. In other words, the intensity signals (generally weak) of the crystalline lens becomes discontinuous, which can be fatal in a case of trying to quantitatively evaluate a turbid condition or the like. Meanwhile, when the polarization mismatch detected between the first OCT data and the second OCT data is eliminated according to the present example, such a gap is not generated.

Further, in the description above, since it is possible to detect the FPN signal with high accuracy as the polarization state of the FPN generation optical system is adjusted, it is possible to appropriately perform various types of processing using the FPN signal.

In addition, in the description above, the polarization state related to the OCT data including the crystalline lens is adjusted using the FPN signal, but the invention is not limited thereto, and the polarization state may be adjusted by using the signal intensity of the entire crystalline lens image in the OCT data.

In addition, in the description above, in a case of using the first detector 120*a* and the second detector 120*b*, with respect to each of the OCT data obtained by the first detector 120*a* and the OCT data obtained by the second detector 120*b*, it is possible to acquire each piece of the OCT data with excellent signal intensity by adjusting the polarization state. Naturally, the invention is not limited thereto, and the polarization state may be adjusted only for one piece of the OCT data.

In addition, in a case of using any one of the first detector 120*a* and the second detector 120*b*, for example, the polarization state may be adjusted with respect to the OCT data obtained by the detector used.

<Wide-Angle Fundus Capturing Mode>

The above-described fundus capturing mode may be a wide-angle fundus capturing mode for obtaining the OCT data in a wide-angle region including the fundus central portion and the fundus peripheral portion. In addition, it is also possible to switch between the above-described normal fundus capturing mode and the wide-angle fundus capturing mode. Further, in the wide-angle fundus capturing mode, the scanning range of the measurement light on the fundus by the optical scanner 156 may be set to the wide-angle region including the central portion and the peripheral portion of the fundus. In this case, a lens attachment for wide-angle capturing may be used.

Figure 16:
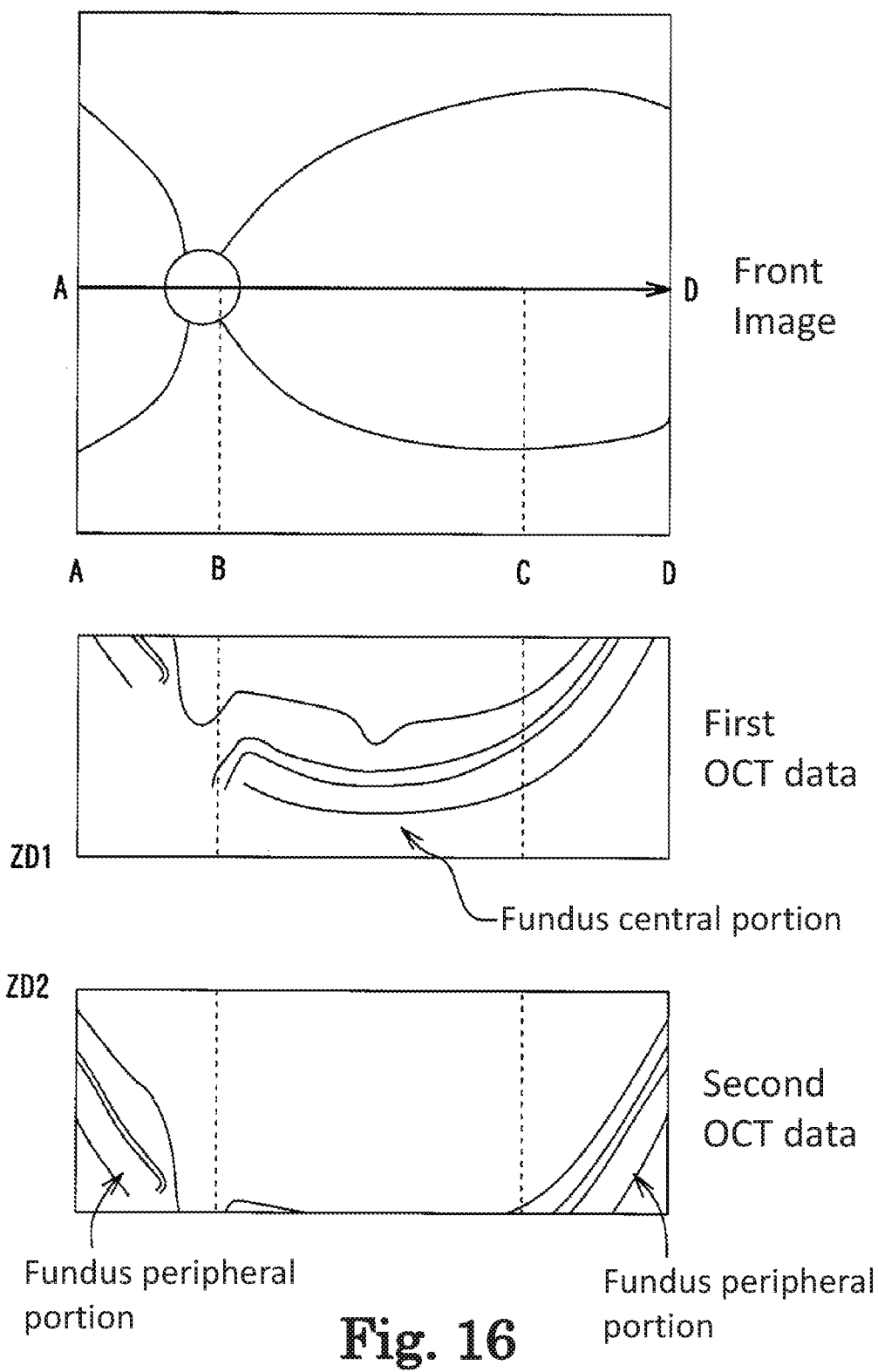
FIG. 16 is a view illustrating an example of the OCT data acquired in a wide-angle fundus capturing mode.

FIG. 16 is a view illustrating an example of the OCT data acquired in the wide-angle fundus capturing mode. In a case where the wide-angle fundus capturing mode is set, the control section 70 may adjust the optical path length of at least one of the measurement light and the reference light, and may set the acquisition region of the OCT data by the first detector 120*a* and the second detector 120*b* to the wide-angle region including the fundus central portion and the fundus peripheral portion. For example, the control section 70 may set the acquisition region of the OCT data by the first detector 120*a* in the fundus central portion, and may set the acquisition region of the OCT data by the second detector 120b in the fundus peripheral portion. In the present example, the first OCT data may be acquired by the first detector 120a and the second OCT data may be acquired by the second detector 120b.

Here, while the eye is spherical with the eyeball center as the center, and the fundus has a concave shape with the fundus central portion as a bottom portion, the measurement light is swiveled around the vicinity of the pupil center and the fundus is scanned. In this case, the optical path length from the scan center to the fundus peripheral portion is shorter than the optical path length from the scanning center to the fundus central portion. Normally, a range in which the capturing is possible in the depth direction when obtaining the OCT data is a predetermined distance from the zero delay position, and in a case where the fundus is scanned at a wide angle, there is a possibility of being deviated from the range in which the capturing is possible in the depth direction.

Here, for example, the optical path length difference between the first reference optical path 110a and the second reference optical path 110b is set in consideration of the optical path length difference between the fundus central portion and the fundus peripheral portion, and the first OCT data including the OCT data of the fundus central portion and the second OCT data including the OCT data of the fundus peripheral portion can be acquired by adjusting the optical path length difference between the measurement light and the reference light with respect to the examinee's eye fundus. In this case, for example, the optical path length of the first reference optical path 110a may be set in accordance with the optical path length of the measurement light from the fundus central portion, and the optical path length of the second reference optical path 10b may be set in accordance with the optical path length of the measurement light from the fundus peripheral portion. In this case, considering the eyeball shape, the reference optical path 110b that corresponds to the fundus peripheral portion may be set to have a shorter optical path length than that of the reference optical path 110a that corresponds to the fundus central portion. Naturally, depending on the situation, the reference optical path 110b that corresponds to the fundus peripheral portion may be set to have a longer optical path length than that of the reference optical path 110a that corresponds to the fundus central portion.

For example, the OCT data of the fundus peripheral portion included in the second OCT data may be the OCT data in which the OCT data of the fundus central portion included in the first OCT data is continuous in at least one of the transverse direction and the depth direction at the end portion. In this case, for example, the OCT data of the fundus peripheral portion included in the second OCT data may be the OCT data in which some parts of each piece of the OCT data overlap each other in at least any one of the transverse direction and the depth direction, and which is continuous at the end portion. In addition, the optical path length difference between the first reference optical path 110a and the second reference optical path 110b when obtaining the OCT data in the wide-angle region may be fixed or may be variable.

For example, the first OCT data may include the OCT data in a first fundus region including at least the macular portion and the papilla portion of the fundus, and the second OCT data may include the region outside the both end portions of the first fundus region, respectively. In addition, not being limited thereto, the first OCT data may include the OCT data in the first fundus region including at least the macular portion of the fundus, and the second OCT data may include the region outside the both end portions of the first fundus region, respectively.

For example, the first OCT data and the second OCT data may have different data acquisition regions on the examinee's eye in the depth direction, and in this case, between the first OCT data and the second OCT data, the optical path length difference between the first reference optical path 110a and the second reference optical path 110b may be set such that some parts of the acquisition region on the examinee's eye overlap each other in the depth direction. According to this, it is possible to smoothly perform linking processing when combining the first OCT data and the second OCT data.

Figure 17:
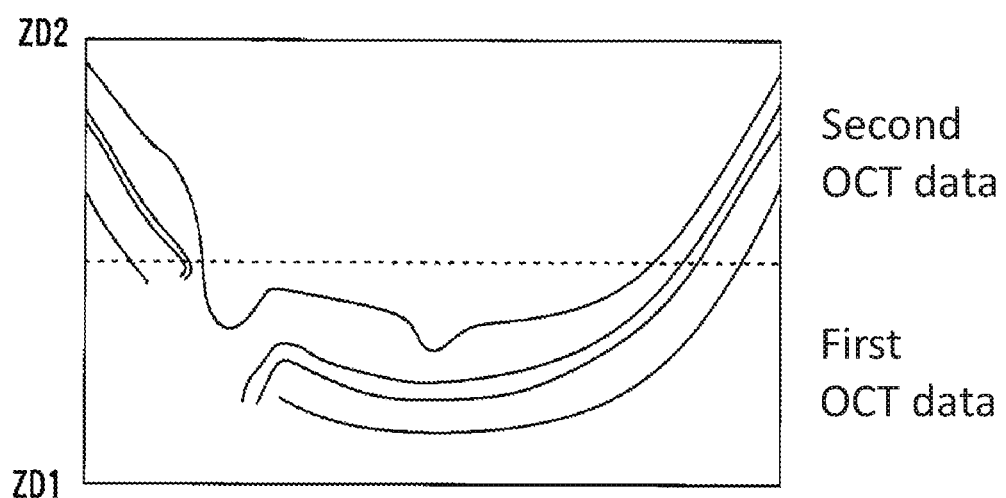
FIG. 17 is a view illustrating an example in a case of combining the OCT data acquired in the wide-angle fundus capturing mode.

FIG. 17 is a view illustrating an example in a case of combining the OCT data acquired in the wide-angle fundus capturing mode. The control section 70 may acquire the wide-angle OCT data based on the first OCT data and the second OCT data, for example, by combining the first OCT data and the second OCT data. In this case, the first OCT data and the second OCT data may be combined so as to be continuous in the depth direction.

In this case, the control section 70 may perform the composition processing using the above-described FPN signal, and the optical path length of the FPN generation optical system 200 may be set such that the optical path length of the measurement light from the central portion and the peripheral portion of the fundus and the optical path length of the measurement light that has passed through the FPN generation optical system 200 are identical to each other.

In a state where the optical path length difference between the measurement light and the reference light is set such that the first OCT data including the OCT data of the fundus central portion and the second OCT data including the OCT data of the fundus peripheral portion can be acquired, the FPN generation optical system 200 may be set such that the FPN signal is included in each piece of the OCT data.

In addition, the composition processing is not limited to the processing using the FPN, and for example, the control section 70 may regulate the positional relationship between the first OCT data and the second OCT data by matching processing using the overlapping region between the first OCT data and the second OCT data, and may perform the data composition. In addition, the control section 70 may regulate the positional relationship between the first OCT data and the second OCT data using the optical path length difference between the first reference optical path 110a and the second reference optical path 110b, and may perform the data composition. At this time, in a case where there is the overlapping region, a signal with higher sensitivity may be adopted, or a side with less noise artifact may be adopted. In addition, processing, such as various types of smoothing may be performed in a connecting portion such that a sudden change does not occur in the connecting portion.

<Wide-Angle Capturing with One Time B Scan>

The control section 70 may control the optical scanner 156, may scan the measurement light in the wide-angle region including the central portion and the peripheral portion of the fundus by B scan performed one time, and may acquire first B scan OCT data and second B scan OCT data (refer to FIG. 16).

For example, in a case where B scan is performed one time from a start point A to an end point D in the horizontal direction, when the fundus region from the start point A to the vicinity of the point B is scanned, based on the output signal from the second detector 120b, OCT data by the reflected light from the fundus peripheral portion (left side)

and the reference light are acquired. Also, based on the output signal from the first detector 120*a*, the OCT data by the reflected light from the fundus central portion close to the fundus peripheral portion (left side) and the reference light is acquired.

Next, when the fundus region from the vicinity of a point B to the vicinity of a point C is scanned, based on the output signal from the first detector 120*a*, the OCT data by the reflected light from the central portion and the reference light is acquired. Furthermore, when the fundus region from the vicinity of the point C to the end point D is scanned, based on the output signal from the second detector 120*b*, the OCT data by the reflected light from the peripheral portion (right side) and the reference light is acquired. In addition, based on the output signal from the first detector 120*a*, the OCT data by the reflected light from the fundus central portion close to the fundus peripheral portion (right side) and the reference light is acquired.

According to the above-described control, the B scan OCT data in the wide-angle region can be acquired smoothly. In this case, the wide-angle B scan OCT data may be acquired by combining the acquired first OCT data and second OCT data.

In addition, B scans may be performed with respect to a plurality of wide-angle regions on the fundus respectively (for example, cross scanning, multiline scanning, or radial scanning). In addition, not being limited thereto, B scan may be performed by dividing the wide-angle region including the fundus central portion and the fundus peripheral portion plural times, and the first B scan OCT data and the second B scan OCT data may be acquired.

In addition, the control section 70 may scan the measurement light in the wide-angle region including the fundus central portion and the fundus peripheral portion at each scanning line by one time of raster scan, and may acquire first three-dimensional OCT data and second three-dimensional OCT data. In this case, measurement light is scanned with respect to each of a plurality of scan lines that configure the raster scan respectively. Each of the scan lines may have a scan range that corresponds to the wide-angle region respectively. According to this, it is possible to smoothly acquire the three-dimensional OCT data in the wide-angle region. In this case, for example, the control section 70 may scan the measurement light plural times with respect to each of the scan lines that configure the raster scan, and based on a plurality of OCT data which temporally varies in each of the scan lines, three-dimensional motion contrast OCT data (OCT angio data) in a wide-angle may be acquired.

In addition, the scanning range in one time B scan is not limited to the scanning range with respect to a front image illustrated in FIG. 16, and it is needless to say that the present example can also be applied even in a case of scanning a wider angle of fundus region. In this case, two reference optical paths may be used, or three or more reference optical paths may be used.

<Optical Path Length Adjustment>

Hereinafter, an example of the optical path length adjustment in the wide-angle fundus capturing mode will be described below. In the present example, for example, the optical path length of the measurement light may be adjusted as the optical member disposed in the measurement optical path is disposed such that the optical path length of the measurement light from the fundus central portion is identical to the optical path length of the reference light from the first reference optical path 110*a*. According to this, at least the OCT data including the fundus central portion is included in the first OCT data obtained based on the output signal from the first detector 110*a*.

In a state where the position of the optical member disposed in the measurement optical path is adjusted such that the OCT data of the fundus central portion is acquired, for example, the control section 70 may adjust the optical path length of the reference light of the second reference optical path 110*b* as the optical member 112 disposed in the second reference optical path 110*b* is disposed such that the optical path length of the measurement light from the fundus peripheral portion and the optical path length of the reference light from the second reference optical path 110*b* are identical to each other. According to this, the OCT data of the fundus peripheral portion is included in the second OCT data obtained based on the output signal from the second detector 110*b*. In addition, in the description above, instead of adjusting the optical path length of the measurement light, the optical path length of the reference light of the first reference optical path 110*a* may be adjusted.

<First Example Regarding Setting of Optical Path Length>

In the first reference optical path 110*a*, the optical path length may be set such that first OCT data is acquired in a state where a choroid layer of the fundus central portion is formed on the farther front side than the zero delay position (refer to FIG. 16). According to this, for example, it is possible to reduce deterioration of a choroid layer image accompanying the sensitivity attenuation in the OCT data in the fundus central portion, and to reduce the mixing of the mirror image (virtual image) and the real image in the first OCT data.

In addition, in the second reference optical path 110*b*, the optical path length may be set such that second OCT data is acquired in a state where the retina of the fundus peripheral portion is formed on the farther inner side than the zero delay position (refer to FIG. 16). According to this, for example, it is possible to reduce deterioration of an image accompanying the decrease in light amount in the fundus peripheral portion, and to reduce the mixing of the mirror image (virtual image) and the real image in the second OCT data.

In addition, in a case of obtaining the OCT data in the wide-angle region, the tendency that the light amount decreases as approaching the periphery appears prominently. This is because the pupil center does not necessarily match the fundus curvature due to the characteristics of the objective optical system, the deviation occurs between the direction of the irradiated light and the direction of the reflected, scattered, and detected light as being deviated from the center. For example, the amount of return light at the position most distant from the center in the fundus peripheral portion is the lowest. This is apparent from the point that, in a fundus OCT image, a saturated portion due to surface reflection is generated in the vicinity of the center at which the surface is irradiated with light perpendicularly and the light matches the direction of a detection system, whereas this phenomenon does not appear in the peripheral portion. As a result, the signal intensity in the fundus peripheral portion tends to be lower than that in the fundus central portion. In general, it is known that the optical performance of a light projecting system is reduced as aberrations is generated as becoming off the axis, and it is possible to say that reduction in the amount of return light at the outermost periphery is inevitable from the viewpoint of the influence thereof. In addition, since the influence contributes not only to a linear shape but also at least to the square of the half angle of view, the influence appears prominently as the system is widened.

Here, considering the tendency that the amount of return light decreases as approaching the periphery and the sensitivity characteristics in the depth direction that the sensitivity increases as approaching the zero delay position, by setting the optical path length such that the second OCT data is acquired in a state where the retina of the fundus peripheral portion is formed on the father inner side than the zero delay position, it is possible to increase the sensitivity as approaching the periphery, and thus, it is possible to reduce the influence of the decrease in light amount in the fundus peripheral portion.

In addition, the first OCT data is acquired in a state where the choroid layer in the fundus central portion is formed on the farther front side than the zero delay position, the second OCT data is acquired in a state where the retina in the fundus peripheral portion is formed on the farther inner side than the zero delay position, and accordingly, it is possible to reduce the mixing of the mirror image and the real image in both of the first OCT data and the second OCT data, and to obtain the entire OCT data in the wide-angle region with excellent signal intensity.

<Second Example Regarding Setting of Optical Path Length>

Figure 18:
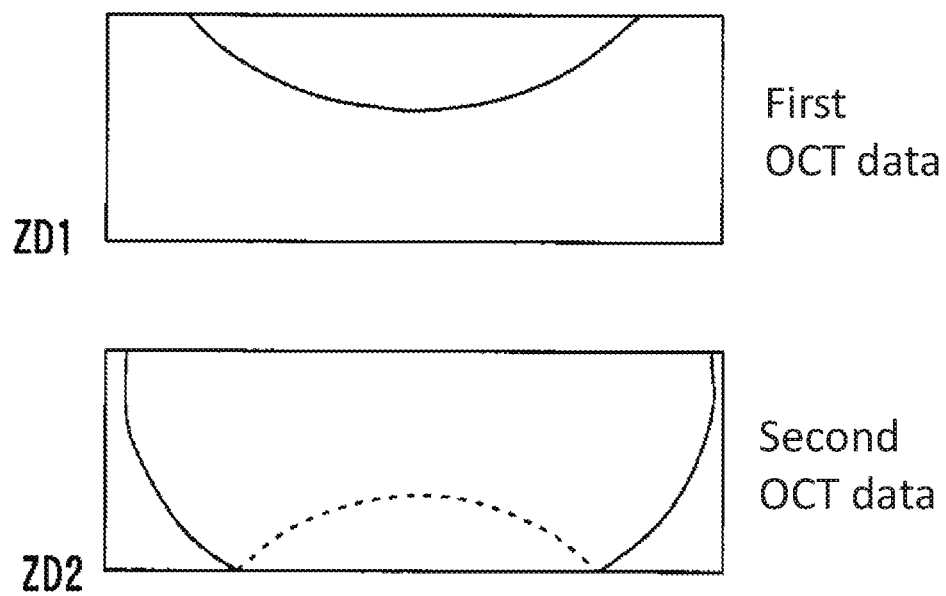
FIG. 18 is a view illustrating another example of the OCT data acquired in the wide-angle fundus capturing mode.

In addition, in the description above, a method for reducing the mixing of the mirror image and the real image is exemplified, but the invention is not limited thereto. FIG. 18 is a view illustrating another example of the OCT data acquired in the wide-angle fundus capturing mode. For example, when acquiring the second OCT data, the optical path length may be set such that the choroid layer in the fundus peripheral portion is formed on the farther front side than the zero delay position, and the retina in the fundus central portion is formed on the farther inner side than the zero delay position. In this case, the mixing of the mirror image when the fundus central portion is scanned and the real image when the fundus peripheral portion is scanned is generated, but since the fundus is a planar tissue with a relatively small thickness, and thus, the overlapping range is small, and there can be a case where the fundus can be used in fundus diagnosis by appropriately cutting out the use area.

Figure 19:
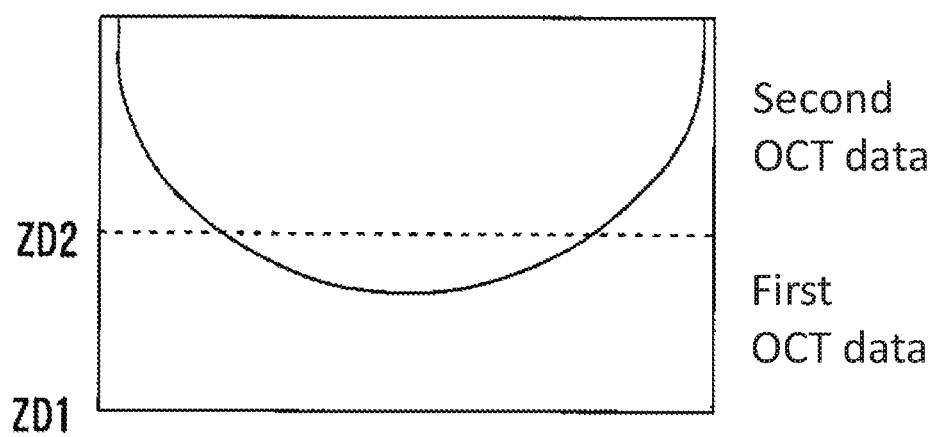
FIG. 19 is a view illustrating an example in a case of combining the OCT data exemplified in FIG. 18.

FIG. 19 is a view illustrating an example in a case of combining the OCT data exemplified in FIG. 18. For example, when combining the first OCT data and the second OCT data, by combining the data of the peripheral part in the second OCT data and the data of the center part in the first OCT data, it is possible to reduce the influence of the mirror image.

In addition to acquiring the second OCT data as described above, for example, when acquiring the first OCT data, the optical path length may be set such that the choroid layer in the fundus central portion is formed on the farther front side than the zero delay position. According to this, since the choroid layer side has high sensitivity in each piece of the OCT data, the tissue change in the choroid layer can be more easily discriminated in the wide-angle region.

<Third Example Regarding Setting of Optical Path Length>

For example, when acquiring the first OCT data, the optical path length may be set such that the retina in the fundus central portion is formed on the farther inner side than the zero delay position, and the choroid layer in the fundus peripheral portion is formed on the farther front side than the zero delay position. In this case, the mixing of the mirror image when the fundus peripheral portion is scanned and the real image when the fundus central portion is scanned is generated, but since the fundus is a planar tissue with a relatively small thickness, and thus, the overlapping range is small, and there can be a case where the fundus can be used in fundus diagnosis.

In addition, for example, when combining the first OCT data and the second OCT data, by combining the data of the peripheral part in the second OCT data and the data of the center part in the first OCT data, it is possible to reduce the influence of the mirror image.

In addition to acquiring the first OCT data as described above, for example, when acquiring the second OCT data, the optical path length may be set such that the choroid layer in the fundus peripheral portion is formed on the farther inner side than the zero delay position. According to this, since the retina side has high sensitivity in each piece of the OCT data, the tissue change in the retina can be more easily discriminated in the wide-angle region.

<Utilization of Plurality of Detectors in Wide-Angle Capturing>

Figure 20:
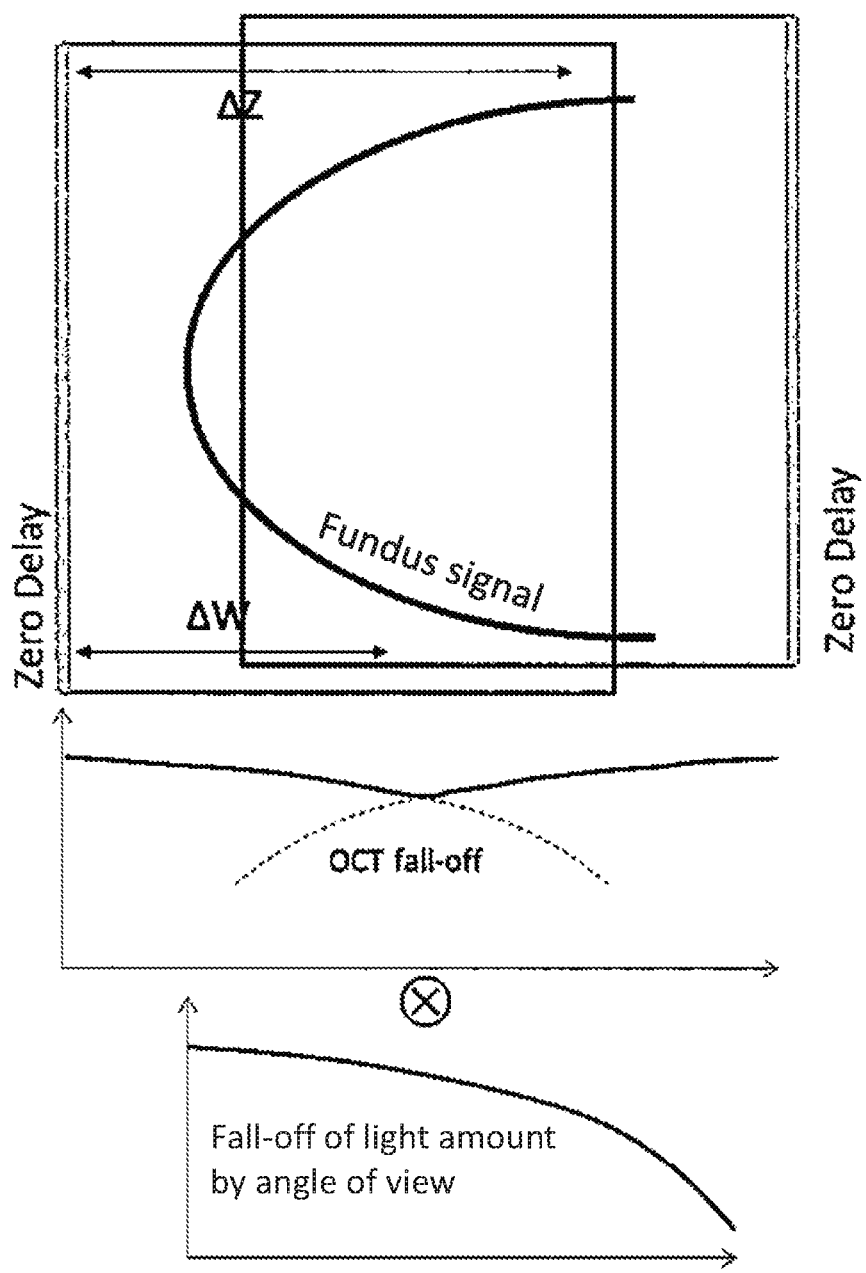
FIG. 20 is a view illustrating an example in a case where the OCT data of a fundus central portion and a fundus peripheral portion is obtained using a plurality of reference optical paths and a plurality of detectors.
Figure 21:
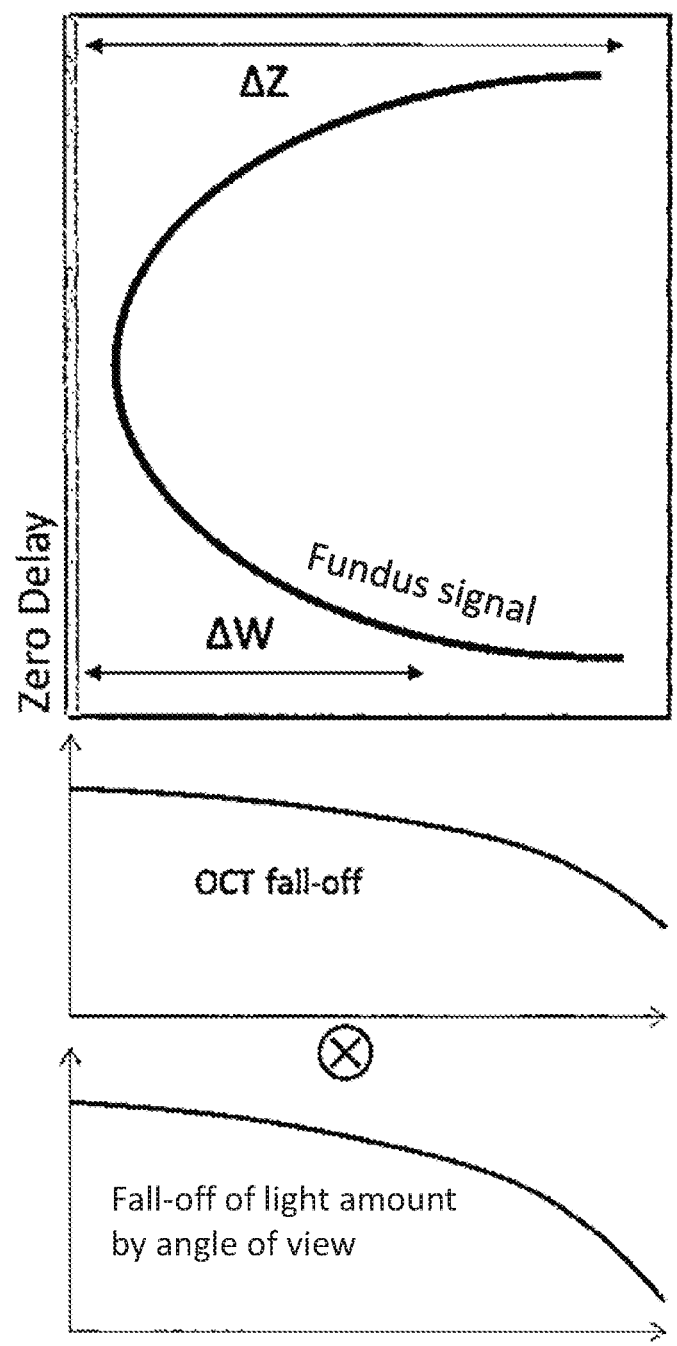
FIG. 21 is a view illustrating an example according to a first configuration in a case where the OCT data of the fundus central portion and the fundus peripheral portion is obtained using one reference optical path and one detector.
Figure 22:
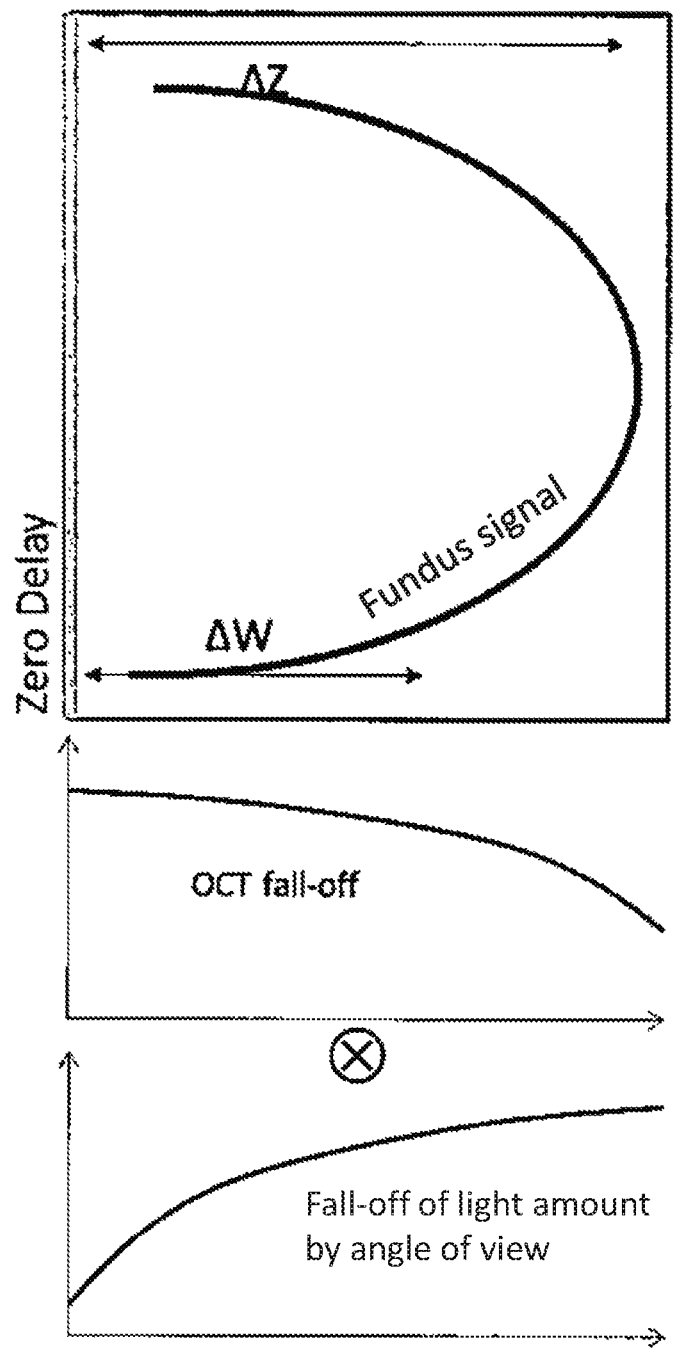
FIG. 22 is a view illustrating an example according to a second configuration in a case where the OCT data of the fundus central portion and the fundus peripheral portion is obtained using one reference optical path and one detector.

FIG. 20 is a view illustrating an example in a case where the OCT data of the fundus central portion and the fundus peripheral portion is obtained using a plurality of reference optical paths and a plurality of detectors. FIGS. 21 and 22 are views illustrating an example in a case where the OCT data of the fundus central portion and the fundus peripheral portion is obtained using one reference optical path and one detector. In addition, in FIGS. 20 to 22, ΔW indicates a region in which the capturing is possible while maintaining a predetermined sensitivity with respect to the sensitivity at the zero delay position.

In the present example, by providing the reference optical path and the detector for obtaining the OCT data of the fundus central portion and the reference optical path and the detector for obtaining the OCT data at the fundus peripheral portion, respectively, it is possible to simultaneously obtain the OCT data of the fundus central portion and the fundus peripheral portion with excellent signal intensity (refer to FIG. 20).

In this case, the first OCT data is acquired by one of the first detector 120a and the second detector 120b, and the second OCT data may be acquired by the other of the first detector 120a and the second detector 120b.

In addition, in a case of simultaneously acquiring the OCT data of the fundus central portion and the fundus peripheral portion using only one reference optical path and one detector, there can be a case where the fundus central portion is disposed on the farther front side than the zero delay position as a first configuration (refer to FIG. 21), or a case where the fundus peripheral portion is disposed on the farther inner side than the zero delay position as a second configuration (refer to FIG. 22). In this case, there is influence of the sensitivity attenuation characteristics in the depth direction in which the sensitivity is attenuated as being separated from the zero delay position, and the light amount decrease characteristics that the light amount decreases as approaching the periphery.

In a case of the first configuration, the retina and choroid layer in the vicinity of the center are seen with relatively excellent contrast, but the image quality of the fundus peripheral portion largely decreases due to the dual effect caused by the sensitivity attenuation characteristics and the light amount decrease characteristics. Therefore, even when the capturing is performed at a wide angle, the sensitivity is not sufficient in the wide-angle region, it is needless to say that improvement of the diagnostic ability by the wide-angle is limited. Meanwhile, in a case of the second configuration, the retina and the choroid layer in the vicinity are seen with relatively excellent contrast, but the image quality at the macular portion and the papilla portion which are important in fundus disease, largely deteriorates (refer to FIG. 21). In recent years, studies have been known that structural changes due to ocular diseases appear in the vicinity of the choroid layer prior to retina, and in a case of the second configuration, the diagnostic ability on the choroid layer side deteriorates by setting the angle to a wide-angle.

In addition, in the above-described configuration, the detectors are provided in the fundus central portion and the fundus peripheral portion respectively, but the detector may be used both in the fundus central portion and the fundus peripheral portion, and in this case, for example, a configuration may be adopted in which a plurality of reference optical paths may be selectively switched by an optical switch or the like. Even with such a configuration, it is possible to obtain the OCT data of fundus central portion and fundus peripheral portion with excellent signal intensity.

<Use in Combination with Anterior Ocular Segment Capturing Mode>

In addition, in the present example, by using the reference optical path and the detector for obtaining the OCT data of the fundus central portion and the reference optical path and the detector for obtaining the OCT data at the fundus peripheral portion in acquiring the OCT data of the anterior ocular segment including the front surface and rear surface of the cornea and the crystalline lens, it is possible to obtain the OCT data of the central portion and the peripheral portion of the fundus and the OCT data of the anterior ocular segment including the front surface and the rear surface of the cornea and the crystalline lens with excellent signal intensity, and it is possible to obtain the OCT data of the entire eyeball with excellent signal intensity. In addition, the anterior ocular segment capturing mode has been described above, and a detailed description thereof will be omitted.

In addition, by using separate detectors for the cornea and the crystalline lens, simultaneous detection becomes possible, but the detector may be used both for the cornea and the crystalline lens, and in this case, for example, a configuration may be adopted in which the plurality of reference optical paths is selectively switched by an optical switch or the like.

<Alignment Detection Using OCT Signal>

For example, the control section 70 may adjust the optical path length of at least one of the measurement light and the reference light, may set the acquisition region of the OCT data by one of the first detector 120*a* and the second detector 120*b* to the anterior ocular segment including at least one of the cornea and the pupil (or iris), and may detect the relative position information of the apparatus main body with respect to the examinee's eye based on the position of the characteristic part on the OCT data. In this case, the optical path length difference between the measurement light and the reference light in the OCT optical system 100 may be acquired in advance (may be stored in the memory in advance, or may be detected based on the position or the like of the optical member), and since the zero delay position is already known, by detecting the position of the characteristic part with respect to the zero delay position, it is possible to detect relative position information of the apparatus main body with respect to the examinee's eye.

As the relative position information, for example, a working distance of the apparatus main body with respect to the examinee's eye may be detected, the distance in the up-down and left-right directions of the apparatus main body with respect to the examinee's eye may be detected, or the position of the apparatus main body with respect to the examinee's eye may be three-dimensionally detected. In this case, for example, the shift amount from the appropriate alignment position may be detected.

For example, the control section 70 may analyze the OCT data of the anterior ocular segment, may detect the position of the characteristic part (for example, the cornea vertex and the pupil center) of the examinee's eye, and may perform automatic alignment for automatically moving the apparatus main body to the detected characteristic part. In this case, the control section 70 may detect the position of the characteristic part three-dimensionally and perform three-dimensional automatic alignment with respect to the detected characteristic part. According to this, since the three-dimensional position can be detected by the OCT data with high accuracy, it is possible to perform the alignment with respect to the examinee's eye with high accuracy.

In a case of detecting the characteristic part, for example, after performing the image processing, such as edge detection, an image region that corresponds to the characteristic part may be searched, and a position at which the image region that corresponds to the characteristic part is detected may be referred to as a position of the characteristic part. In addition, in the automatic alignment control, a driving mechanism for moving the apparatus main body three-dimensionally may be provided.

Hereinafter, an example of a case where the alignment detection is performed using the anterior ocular segment data will be described. For example, the control section 70 controls the optical scanner 156 and repeatedly performs cross scanning with respect to the examinee's eye anterior ocular segment. The cross scanning may be a scan pattern in which each of the scan lines is orthogonal to each other, and may be, for example, a scan pattern in which the line scanning in the X direction and the line scanning in the Y direction are orthogonal to each other.

Figure 23:
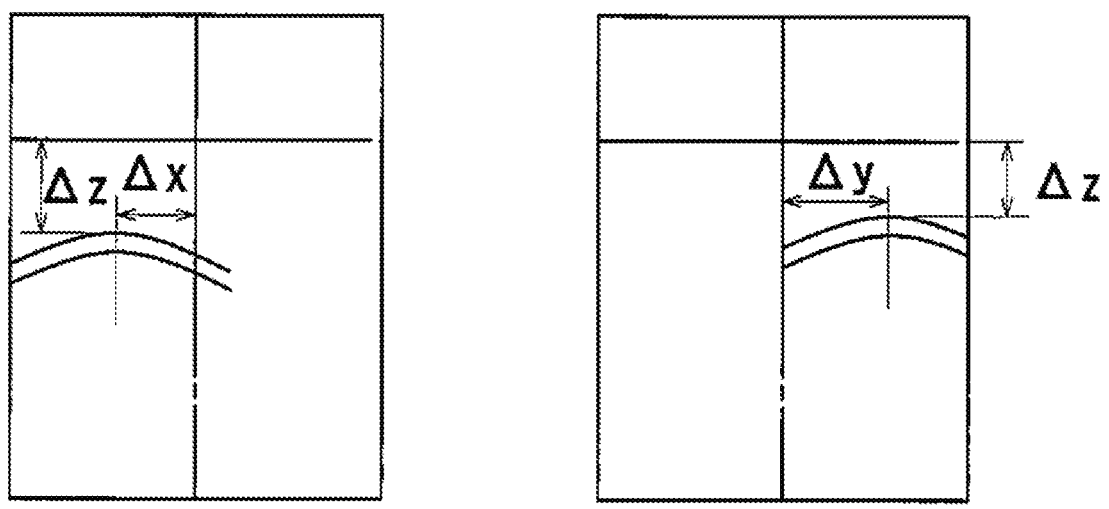
FIG. 23 is an example of each piece of OCT data acquired by cross scanning before alignment is completed.
Figure 24:
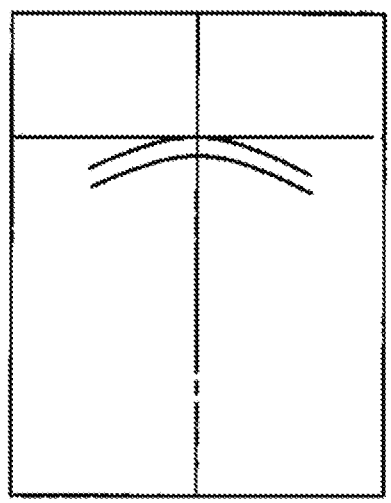
FIG. 24 is an example of each piece of OCT data acquired by cross scanning when alignment is completed.
Figure 24:
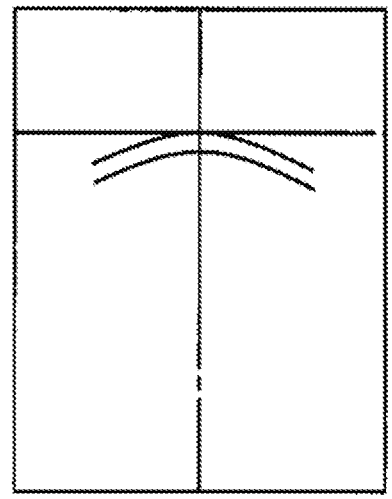

FIGS. 23 and 24 are examples of each piece of the OCT data acquired by the cross scanning, the left view of FIG. 23 is the OCT data acquired by line scanning in the X direction, and the right view of FIG. 23 is the OCT data acquired by the line scanning in the Y direction. FIG. 23 is an example before the alignment is completed, and FIG. 24 is an example when the alignment is completed.

In this case, at the alignment appropriate position, the optical path length or the like of the optical scanner 156 (for example, the center voltage of the galvanometer) and the OCT optical system 100 is adjusted such that the characteristic part in the OCT data (for example, cornea vertex) is formed at a predetermined position in the OCT data. The optical disposition at the time of adjustment and the coordinate data on the predetermined position may be stored in advance in the memory. The alignment appropriate position may be, for example, an alignment position at which the optical axis of the OCT optical system 100 and the distance in the front-back direction are appropriate with respect to the examinee's eye.

For example, the control section 70 may detect the position of the characteristic part in the OCT data by image processing and perform automatic alignment based on the deviation amount of the characteristic part with respect to the preset predetermined position. In this case, the displacement amount in the X direction may be detected from the OCT data obtained by the line scanning in the X direction, and the deviation amount in the Y direction may be detected from the OCT data obtained by the line scanning in the Y direction. In addition, with respect to the deviation amount in the Z direction, the OCT data obtained by at least one of the line scanning in the X direction and the line scanning in the Y direction may be used.

The rough positioning until the OCT data of the anterior ocular segment is acquired may be automatically performed based on a capturing signal from an image capture element for the anterior ocular segment observation (not illustrated). For the automatic alignment using the image capture element for the anterior ocular segment observation, an alignment index projected on the anterior ocular segment may be used.

In addition, the control section 70 may perform rough alignment and severe alignment by changing the scanning range. For example, in the control section 70, when the rough alignment is performed, the scanning angle of view of the measurement light may increase, and when performing the severe alignment, the scanning angle of view of the measurement light may be narrowed.

In addition, in the description above, a case of cross scanning was exemplified, but it is possible to perform alignment to some extent even with scanning in one direction. For example, the control section 70 may perform the automatic alignment in the X direction such that a tomogram of the cornea is bilaterally symmetric in the OCT data obtained by the line scanning in the X direction, and then in the normal direction (for example, Y direction), the apparatus main body may be moved until the cornea curvature becomes the maximum.

In addition, in the description of FIG. 23, a case where the cornea vertex is set as the characteristic part has been exemplified, but the invention is not limited thereto, and for example, by detecting the iris part by the image processing, the pupil position and the pupil diameter may be detected, and the automatic alignment may be performed based on the detection result of at least one of the pupil position and the pupil diameter.

In a case of performing the alignment detection using the OCT signal, for example, fundus may be set as the acquisition region of the OCT data by the other of the first detector 120*a* and the second detector 120*b*. According to this, the alignment with respect to the fundus can be performed with high accuracy. In addition, the control section 70 may use the relative position information of the apparatus main body with respect to the anterior ocular segment detected as described above and the optical path length difference between the first reference optical path 110*a* and the second reference optical path 110*b*, and may detect the relative position information of the apparatus main body with respect to the examinee's eye fundus. In this case, the position of the fundus on the OCT data may be detected. Further, not being limited to the fundus, as the acquisition region of the OCT data by the other of the first detector 120*a* and the second detector 120*b*, the capturing part different from the fundus may be set, and for example, the crystalline lens may be set.

<Optical Path Length Difference Adjustment Function in Accordance with Depth of Subject>

In addition, in the present example, an optical path length difference changing section may be provided in which at least one of the first reference optical path 110*a* and the second reference optical path 110*b* is disposed and the optical path length difference between the first reference optical path 110*a* and the second reference optical path 110*b* changes. The optical path length difference changing section may be configured to be capable of changing the optical path length of at least one of the first reference optical path 110*a* and the second reference optical path 110*b*.

Figure 25:
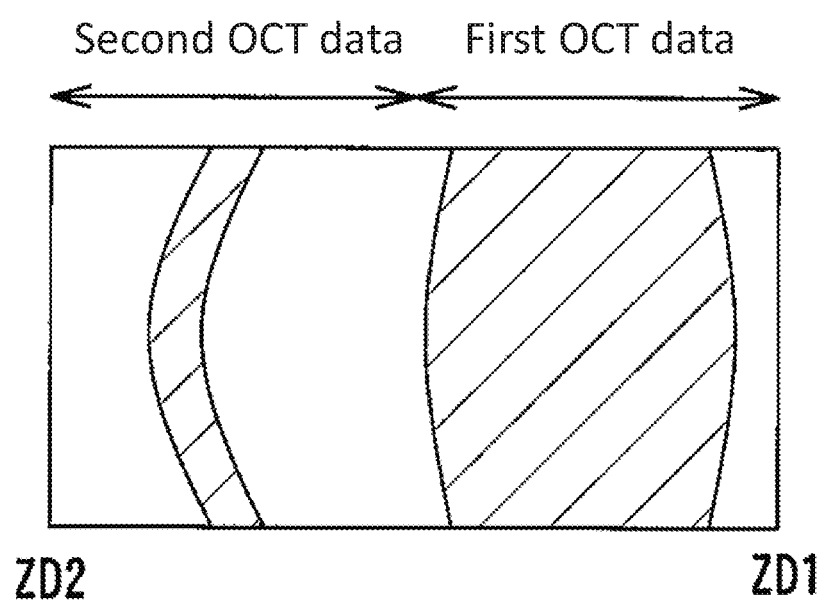
FIG. 25 is a view illustrating an example of combined OCT data after an optical path length difference has been adjusted in accordance with the depth of the test object.

FIG. 25 is a view illustrating an example of the combined OCT data after the optical path length difference has been adjusted in accordance with the depth of the subject. In this case, the control section 70 may acquire the combined OCT data that corresponds to the predetermined part (for example, anterior ocular segment) of the examinee's eye by combining the first OCT data and the second OCT data which are acquired after being changed by the optical path length difference changing section. Accordingly, it is possible to acquire excellent combined OCT data regardless of the depth of the predetermined part of the examinee's eye.

There is a possibility that the depth range (range in which the capturing is possible) of the combined OCT data set in advance is not appropriate for the depth range of the anterior ocular segment to be acquired. For example, in a case where the depth range of the preset combined OCT data is set to have a depth within a range in which the capturing is sufficiently possible from the cornea front surface of the general eye to the rear face of the crystalline lens, the following situation can occur. For example, in a case of capturing the examinee's eye which is short from the cornea front surface to the crystalline lens rear surface, such as the eyes of children, shorter eyes than normal eyes, or pathological eyes (the thickness of the crystalline lens, the thickness of the anterior chamber, and the shape of the cornea are not common) including IOL eyes, the position of the fixation target changes or the like, and in a case of capturing the anterior ocular segment of the eyes which are in the near-looking state (thick crystalline lens) and in the far-looking state (thin crystalline lens) from the cornea front surface to the crystalline lens rear surface, the distance to the cornea and the crystalline lens rear surface with respect to the zero delay position is separated. Accordingly, due to the influence of sensitivity attenuation, there is a possibility that the anterior ocular segment image cannot be excellently formed.

Here, for example, based on the OCT data of the anterior ocular segment once updated in real time, the control section 70 may detect at least one of the position (for example, the cornea position) of the shallowest characteristic part in the anterior ocular segment included in one piece of the OCT data and the position (for example, the position of the crystalline lens rear surface) of the most shallow characteristic part included in the other piece of the OCT data, by the image processing. Next, the control section 70 may control the optical path length difference changing section, and may change the optical path length difference between the first reference optical path 110*a* and the second reference optical path 110*b* such that the detected characteristic part is disposed at a predetermined position with respect to the zero delay position. According to this, for example, since the distance from the zero delay position to the characteristic part of the anterior ocular segment can be made to be in the vicinity of the optimum part, in the above-described anterior ocular segment capturing mode, in a case of combining the first OCT data and the second OCT data, the combined anterior ocular segment OCT data with higher sensitivity can be obtained.

In addition, in a case of combining the first OCT data and the second OCT data, for example, the FPN may be used. In addition, in a case where the optical path length difference is adjusted, the FPN can be used for composition as long as the FPN is in the range in which the FPN is generated within the depth range of the first OCT data and the second OCT data.

<Switching Function Between Entire Anterior Ocular Segment Capturing and Crystalline Lens Capturing>

In the above-described anterior ocular segment capturing mode, a first anterior ocular segment capturing mode for capturing the entire anterior ocular segment and a second anterior ocular segment capturing mode for capturing the crystalline lens may be provided.

For example, in the first anterior ocular segment capturing mode, the control section 70 may adjust the optical path length difference between the first reference optical path 110*a* and the second reference optical path 110*b* such that one of the first OCT data based on the first detector 120*a* and the second OCT data based on the second detector 120*b* is acquired as the OCT data including the cornea and the crystalline lens front surface, and the other of the first OCT data based on the first detector 120*a* and the second OCT data based on the second detector 120*b* is acquired as the OCT data including the crystalline lens rear surface (for example, refer to FIG. 4).

Figure 26:
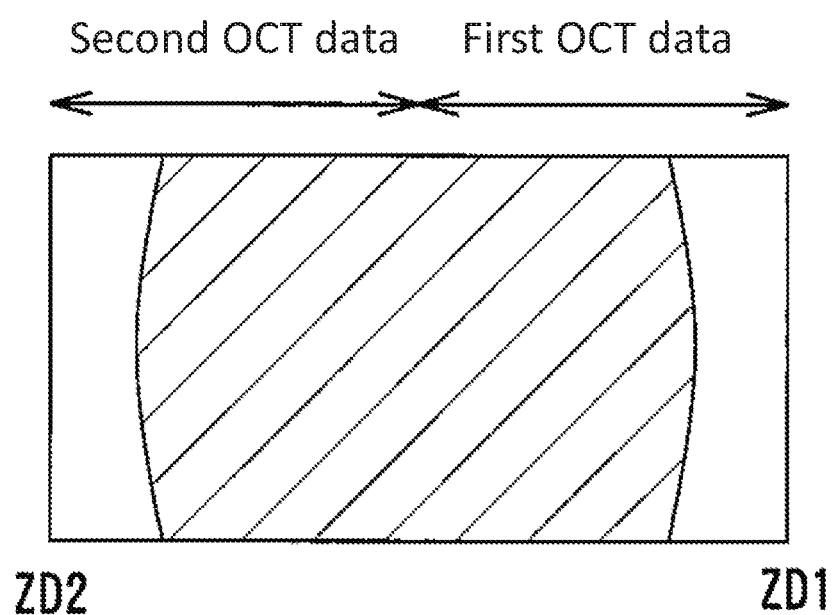
FIG. 26 is a view illustrating an example of the OCT data obtained in the second anterior ocular segment capturing mode for capturing the crystalline lens.

FIG. 26 is a view illustrating an example of the OCT data obtained in the second anterior ocular segment capturing mode for capturing the crystalline lens. For example, in the second anterior ocular segment capturing mode, the control section 70 may adjust the optical path length difference between the first reference optical path 110*a* and the second reference optical path 110*b* such that one of the first OCT data based on the first detector 120*a* and the second OCT data based on the second detector 120*b* is acquired as the OCT data including the crystalline lens front surface, and the other of the first OCT data based on the first detector 120*a* and the second OCT data based on the second detector 120*b* is acquired as the OCT data including the crystalline lens rear surface. In this case, the optical path length difference may be set such that the zero delay position is disposed between the cornea and the crystalline lens front surface.

The control section 70 may acquire the combined anterior ocular segment OCT data with a wide-angle range including the cornea and the crystalline lens front surface and rear surface by combining the first OCT data and the second OCT data acquired in the first anterior ocular segment capturing mode. In addition, the control section 70 may acquire the local combined crystalline lens OCT data including the crystalline lens front surface and rear surface by combining the first OCT data and the second OCT data acquired in the second anterior ocular segment capturing mode.

According to this, for example, in the first anterior ocular segment capturing mode, in a case where the image quality of the crystalline lens front surface is unclear due to a long anterior chamber depth or the like, in the second anterior ocular segment capturing mode, it is possible to ensure the image quality of the crystalline lens front surface.

In addition, in the description above, the SS-OCT is taken as an example, but the invention is not limited thereto, and the present example may be applied to the SD-OCT. In this case, a plurality of spectrometers may be used as a plurality of detectors.

In addition, in the description above, the OCT apparatus for capturing the examinee's eye is taken as an example, but the invention is not limited thereto, and the present embodiment may be applied to the OCT apparatus for capturing the OCT data of the subject. Further, the subject may be a material other than a living body in addition to a living body, such as an eye (anterior ocular segment, fundus, and the like), skin and the like.

What is claimed is:

1. An OCT apparatus comprising:
   an OCT optical system that includes a first optical splitter configured to split light from an OCT light source into a measurement optical path and a reference optical path, and a detector configured to detect an interference signal between measurement light guided to a fundus of an examinee's eye through the measurement optical path and reference light from the reference optical path, and that guides the measurement light to a wide-angle region including a central portion and a peripheral portion of the fundus along one transverse direction in which the measurement light traverses the fundus; and
   an image processor that processes a spectral interference signal output from the OCT optical system to acquire OCT data of the examinee's eye,
   wherein the OCT optical system includes the reference optical path including a first reference optical path having an optical path length set for obtaining OCT data including a central portion of the fundus, and a second reference optical path which is different from the first reference optical path and has an optical path length set for obtaining OCT data including the peripheral portion of the fundus, and
   the image processor
       obtains OCT data including the central portion based on an interference signal between the measurement light guided to the central portion of the fundus and the reference light from the first reference optical path, and
       obtains OCT data including the peripheral portion based on an interference signal between the measurement light guided to the peripheral portion of the fundus and the reference light from the second reference optical path.

2. The OCT apparatus according to claim 1,
   wherein the central portion of the fundus is a region including at least a macular portion and a papilla portion of the fundus, and
   the peripheral portion of the fundus is a region including each region outside both end portions of the central portion in the transverse direction.

3. The OCT apparatus according to claim 2,
   wherein the OCT optical system includes an optical scanner configured to scan the measurement light on the fundus of the examinee's eye, and
   the measurement light is scanned in a wide-angle region including the central portion and the peripheral portion of the fundus by one time B scanning performed by the optical scanner, and OCT data including the central portion and OCT data including the peripheral portion are acquired.

4. The OCT apparatus according to claim 1,
   wherein the detector includes
       a first detector configured to detect an interference signal between the measurement light guided to the central portion of the fundus and the reference light from the first reference optical path, and
       a second detector configured to be different from the first detector and detect an interference signal between the measurement light guided to the peripheral portion of the fundus and the reference light from the second reference optical path.

5. The OCT apparatus according to claim 4, further comprising:
   an FPN generation optical system that includes at least one optical member configured to generate FPN being fixed pattern noise on OCT data, and generate an FPN signal being a noise signal which indicates the FPN, wherein the first detector and the second detector enable to detect the FPN signal, and the image processor enables to simultaneously acquire two OCT data which are respectively corrected based on the FPN signal.

6. The OCT apparatus according to claim 5, further comprising:

a second optical splitter configured to split the measurement optical path into an optical path toward the fundus of the examinee's eye and an optical path of the FPN generation optical system, and split reflected light from the fundus and light from the FPN generation optical system into an optical path toward the first detector and an optical path toward the second detector through the first optical splitter, wherein a light amount split ratio of the reflected light from the fundus by the second optical splitter has a relationship of "the optical path toward the first detector<the optical path toward the second detector through the first optical splitter".

7. The OCT apparatus according to claim 5, further comprising:

an optical path length variable device that is disposed in at least one of the first reference optical path and the second reference optical path, and changes an optical path length of the reference light, wherein, when obtaining OCT data of an anterior ocular segment of the examinee's eye, the optical path length variable device sets the optical path length of the reference light such that the first reference optical path and the second reference optical path have optical path lengths different from each other, and the image processor acquires one of OCT data based on the first detector and OCT data based on the second detector as OCT data including a cornea of the examinee's eye, and acquires the other of the OCT data based on the first detector and the OCT data based on the second detector as OCT data including a crystalline lens of the examinee's eye.

8. The OCT apparatus according to claim 5, further comprising:

an arithmetic processing section configured to obtain combined OCT data by combining OCT data based on the first detector and OCT data based on the second detector based on FPN detected by the first detector and FPN detected by the second detector.

9. The OCT apparatus according to claim 1, wherein an optical path length of the first reference optical path is set such that first OCT data is acquired in a state where a choroid layer of the central portion of the fundus is formed on a farther front side than a zero delay position at which the optical path lengths of the measurement light and the reference light are identical to each other.

10. The OCT apparatus according to claim 1, wherein an optical path length of the second reference optical path is set such that second OCT data is acquired in a state where a retina of the peripheral portion of the fundus is formed on a farther inner side than a zero delay position at which the optical path lengths of the measurement light and the reference light are identical to each other.

11. The OCT apparatus according to claim 1, wherein the detector is configured to detect an interference signal between the measurement light guided to an anterior ocular segment of the examinee's eye through the measurement optical path and the reference light from the reference optical path, an optical path length of the first reference optical path and an optical path length of the second reference optical path are different from each other, one of the first reference optical path and the second reference optical path is set to have an optical path length for obtaining OCT data including a cornea of the examinee's eye, and the other of the first reference optical path and the second reference optical path is set to have an optical path length for obtaining OCT data including a crystalline lens of the examinee's eye.

12. The OCT apparatus according to claim 1, wherein the image processor combines OCT data including the central portion of the fundus and OCT data including the peripheral portion of the fundus to obtain wide-angle OCT data of the fundus.

13. The OCT apparatus according to claim 1, wherein an optical path length difference between the first reference optical path and the second reference optical path is set in consideration of an optical path length difference between the central portion and the peripheral portion of the fundus.

14. The OCT apparatus according to claim 1, further comprising:

an optical path length difference adjuster configured to adjust an optical path length difference between the measurement light and the reference light, wherein the optical path length difference adjuster sets an optical path length of the first reference optical path in accordance with an optical path length of the measurement light from the central portion of the fundus, and sets an optical path length of the second reference optical path in accordance with an optical path length of the measurement light from the peripheral portion of the fundus.

* * * * *